US010883982B2

(12) United States Patent
Schwartz et al.

(10) Patent No.: US 10,883,982 B2
(45) Date of Patent: Jan. 5, 2021

(54) METHODS FOR DETERMINING MOLECULE FOLDING ASSOCIATED WITH PROTEOPATHIES

(71) Applicant: ARIZONA BOARD OF REGENTS ON BEHALF OF THE UNIVERSITY OF ARIZONA, Tucson, AZ (US)

(72) Inventors: Jacob Schwartz, Tucson, AZ (US); John C. Jewett, Tucson, AZ (US); Mahta Moinpour, Tucson, AZ (US); Mehrdad Shadmehr, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/158,074

(22) Filed: Oct. 11, 2018

(65) Prior Publication Data

US 2019/0041385 A1    Feb. 7, 2019

Related U.S. Application Data

(63) Continuation-in-part of application No. PCT/US2017/027444, filed on Apr. 13, 2017, and a continuation-in-part of application No. PCT/US2017/027485, filed on Apr. 13, 2017, and a continuation-in-part of application No. PCT/US2017/027472, filed on Apr. 13, 2017.

(60) Provisional application No. 62/383,310, filed on Sep. 2, 2016, provisional application No. 62/373,278, filed on Aug. 10, 2016, provisional application No. 62/322,148, filed on Apr. 13, 2016.

(51) Int. Cl.
| | | |
|---|---|---|
| G01N 33/68 | (2006.01) |
| G01N 33/533 | (2006.01) |
| G01N 33/58 | (2006.01) |
| C07K 1/113 | (2006.01) |
| C07K 1/13 | (2006.01) |
| G01N 33/60 | (2006.01) |
| G01N 33/532 | (2006.01) |
| G01N 33/52 | (2006.01) |
| G01N 33/574 | (2006.01) |

(52) U.S. Cl.
CPC .......... *G01N 33/533* (2013.01); *C07K 1/1136* (2013.01); *C07K 1/13* (2013.01); *G01N 33/52* (2013.01); *G01N 33/532* (2013.01); *G01N 33/57484* (2013.01); *G01N 33/582* (2013.01); *G01N 33/60* (2013.01); *G01N 33/68* (2013.01); *G01N 33/6803* (2013.01); *G01N 33/6812* (2013.01); *G01N 33/6896* (2013.01)

(58) Field of Classification Search
CPC ...... G01N 33/53; G01N 33/532; G01N 33/68; G01N 33/6896; G01N 33/52; G01N 33/6812
See application file for complete search history.

(56) References Cited

U.S. PATENT DOCUMENTS

| | | |
|---|---|---|
| 9,458,143 B1 | 10/2016 | Jewett et al. |
| 9,593,080 B1 | 3/2017 | Jewett et al. |
| 10,047,061 B2 | 8/2018 | Jewett et al. |
| 10,125,105 B2 | 11/2018 | Jewett et al. |
| 2003/0198940 A1 | 10/2003 | Carlson et al. |
| 2013/0109581 A1 | 5/2013 | Salisbury et al. |
| 2013/0273573 A1 | 10/2013 | Allauzen et al. |
| 2015/0087526 A1 | 3/2015 | Hesselberth |
| 2016/0054322 A1 | 2/2016 | Treiber et al. |
| 2017/0114033 A1 | 4/2017 | Jewett et al. |
| 2017/0320834 A1 | 11/2017 | Jewett et al. |
| 2018/0230106 A1 | 8/2018 | Jewett et al. |

FOREIGN PATENT DOCUMENTS

| | | |
|---|---|---|
| WO | WO2015191735 A1 | 12/2015 |
| WO | WO2016015022 A1 | 1/2016 |
| WO | WO2017027743 A1 | 2/2017 |
| WO | WO2017180889 A1 | 10/2017 |
| WO | WO2017180904 A1 | 10/2017 |
| WO | WO2017180911 A1 | 10/2017 |
| WO | WO2018023130 A1 | 2/2018 |

OTHER PUBLICATIONS

Blokhuis et at. Protein aggregation in amyotrophic lateral sclerosis. Acta Neuropathol. Jun. 2013; vol. 125. No. 6, pp. 777-794.
International Search Report for PCT Application No. PCT/US17/27444 dated Jul. 12, 2017.
International Search Report for PCT Application No. PCT/US17/27485 dated Jul. 17, 2017.
International Search Report for PCT Application No. PCT/US17/27472 dated Sep. 6, 2017.

*Primary Examiner* — Robert C Hayes
(74) *Attorney, Agent, or Firm* — Nguyen Tarbet LLC

(57) ABSTRACT

Methods, systems, and compositions for detecting molecule aggregation, folding, or interactions featuring comparing the amount of labeling of a molecule of interest, such as a protein, in a test sample with an amount of labeling in a control, e.g., a sample wherein the molecule of interest is denatured. If less labeling is present in the test sample as compared to the control sample, the test sample may comprise the molecule of interest in aggregate form, folded form, or interactive form, e.g., interacting with another molecule such as a protein molecule, DNA molecule or RNA molecule. The present invention may be used for detecting or monitoring a disease or condition such as a protein misfolding disease (proteopathy), e.g., amyotrophic lateral sclerosis (ALS), etc.

12 Claims, 10 Drawing Sheets
(10 of 10 Drawing Sheet(s) Filed in Color)

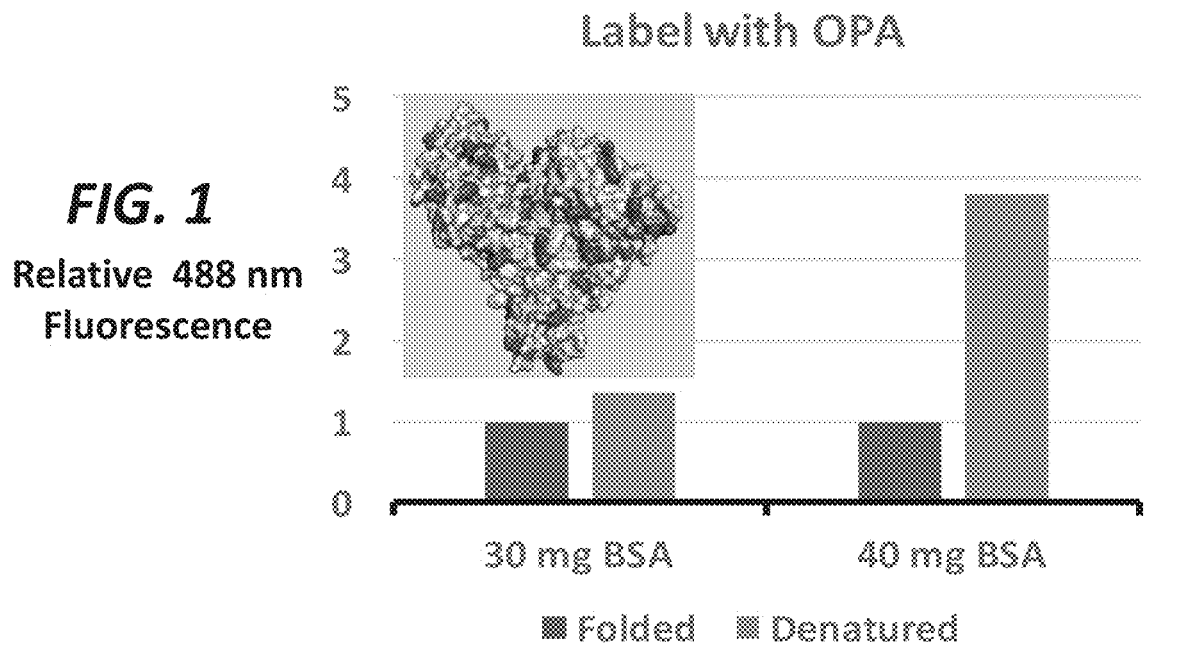
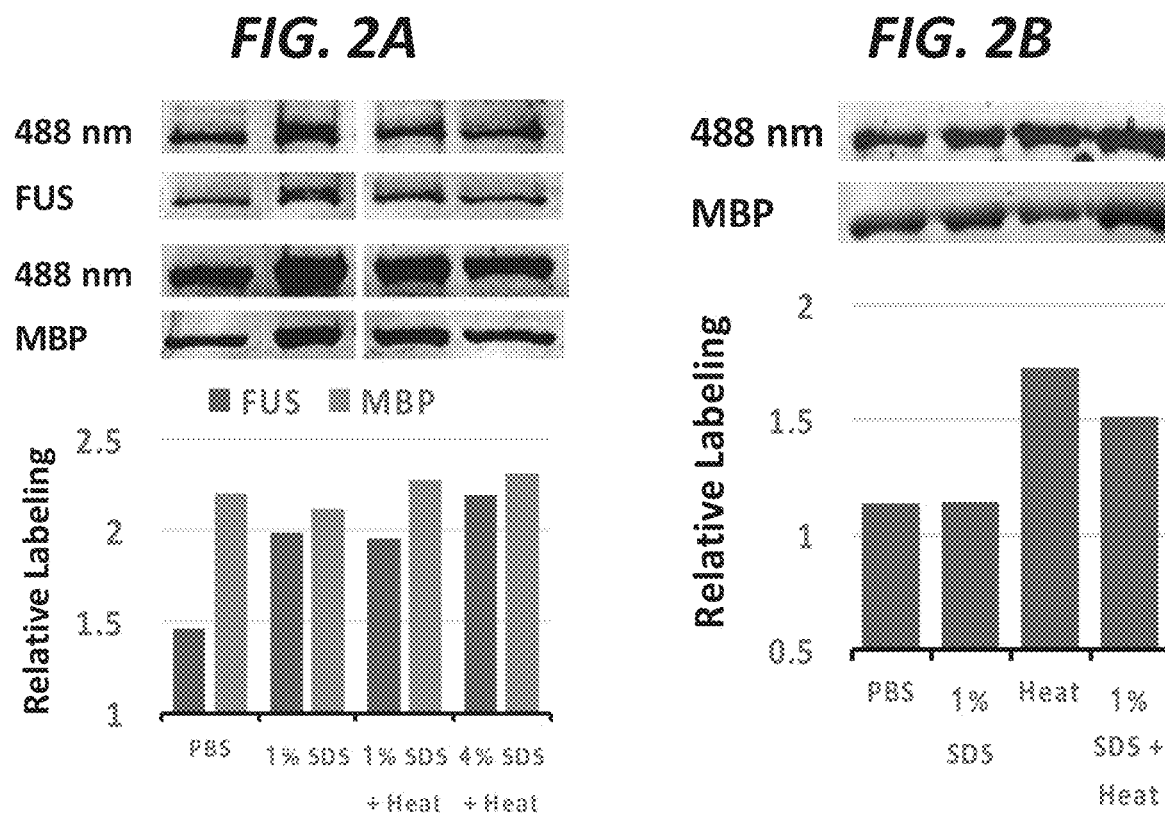

FIG. 3
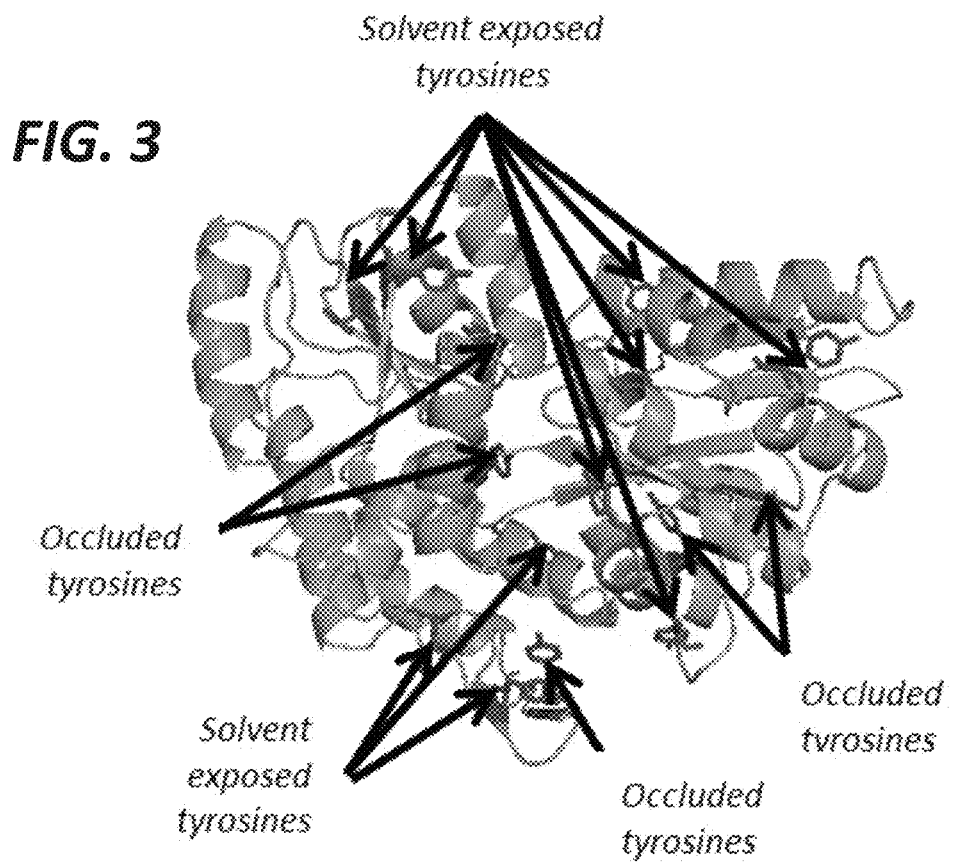
FIG. 4
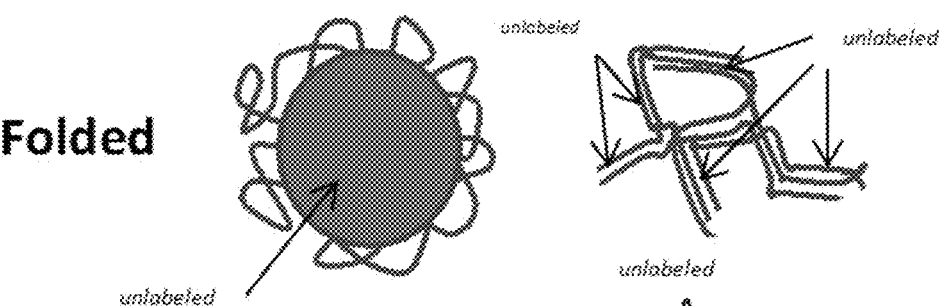
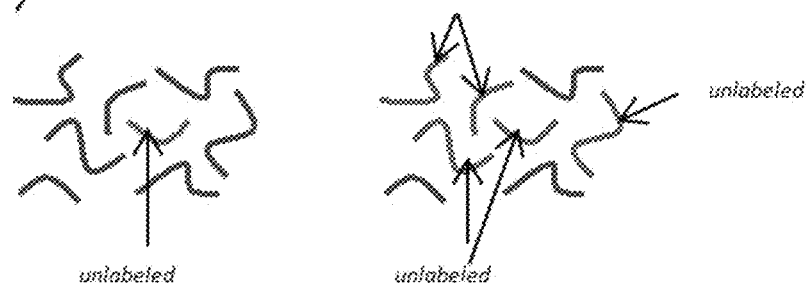

FIG. 6
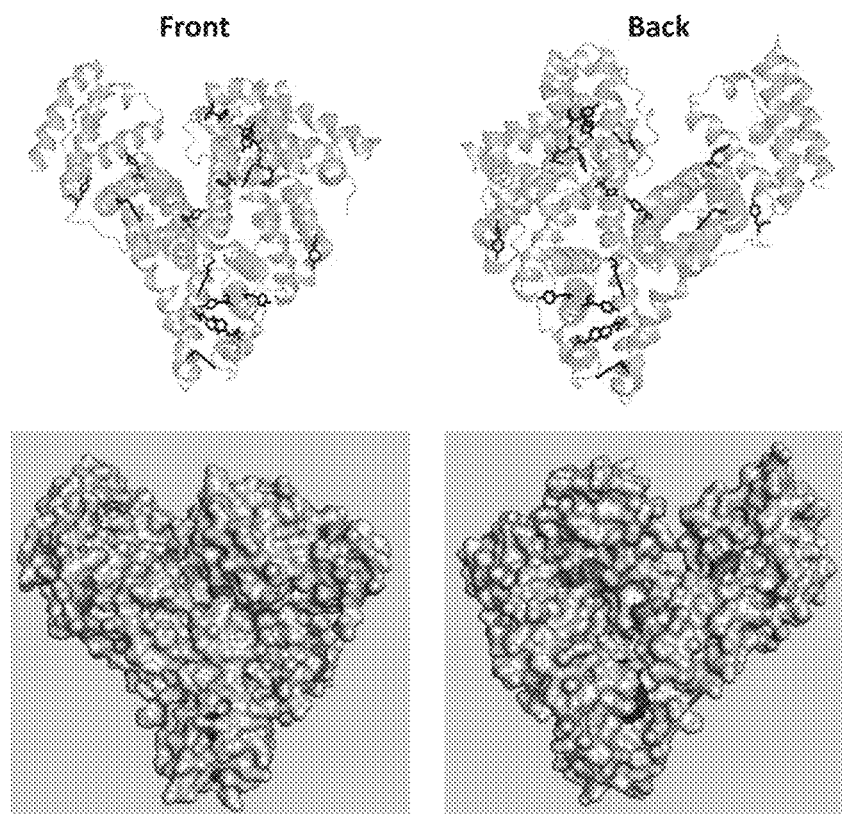
FIG. 7
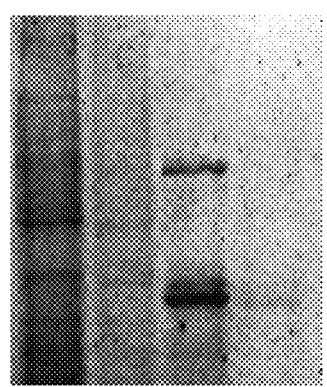
488 nm fluorescence
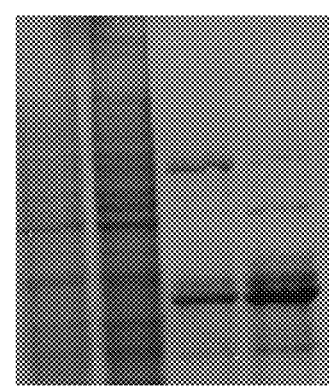
Coommassie
FUS
MBP

METHODS FOR DETERMINING MOLECULE FOLDING ASSOCIATED WITH PROTEOPATHIES

CROSS REFERENCE

This application is a continuation-in-part and claims benefit of PCT Application No. PCT/US17/27444 filed Apr. 13, 2017, is a continuation-in-part and claims benefit of PCT Application No. PCT/US17/27472 filed Apr. 13, 2017, is a continuation-in-part and claims benefit of PCT Application No. PCT/US17/27485 filed Apr. 13, 2017, and claims benefit of U.S. Provisional Patent Application No. 62/322,148 filed Apr. 13, 2016, U.S. Provisional Patent Application No. 62/373,278 filed Aug. 10, 2016, and U.S. Provisional Patent Application No. 62/383,310 filed Sep. 2, 2016, the specification(s) of which is/are incorporated herein in their entirety by reference.

GOVERNMENT SUPPORT

This invention was made with government support under Grant No. R00 NS082376 awarded by NIH. The government has certain rights in the invention.

FIELD OF THE INVENTION

The present invention relates to methods, systems, and compositions for detecting various states of molecules such as but not limited to proteins (or nucleic acids or other molecules), for example, folding or conformational states, interactive states (e.g., interactions between biomolecules), aggregate or bound states, etc. The present invention also relates comparing or evaluating changes in states of said molecules, e.g., changes in protein folding conformations, etc. The methods, systems, and compositions of the present invention may be used for detecting or monitoring aggregates or folding states related to proteopathies (protein misfolding diseases), e.g., Alzheimer's disease, Parkinson's disease, Creutzfeldt-Jacob disease, prion disease, amyloidosis, Huntington's disease, frontotemporal lobar degeneration (FTLD), etc. For example, the methods, systems, and compositions of the present invention may be used for detecting or monitoring aggregates or folding states related to disease states such as amyotrophic lateral sclerosis (ALS).

BACKGROUND OF THE INVENTION

The present invention features methods, systems, and compositions for detecting various states (e.g., assembled states, folding or conformational states, interactive states, aggregate states, bound states, etc.) of molecules. Molecules may include but are not limited to proteins, nucleic acids, or other molecules. For example, the present invention features methods, systems, and compositions for detecting molecules in aggregate states, assembled states, bound or unbound states, folded, unfolded, or misfolded states, interactive or non-interactive states, alternative conformations, etc. The present invention also features comparing or evaluating changes in states of said molecules, e.g., changes in protein folding conformations, changes in aggregation, etc. Further, the methods of the present invention can help study interactions and conformational changes in intrinsically disordered proteins and domains. Without wishing to limit the present invention to any theory or mechanism, it is believed that intrinsically disordered proteins or domains cannot easily be studied using current standard techniques.

As an example, the protein Fused in Sarcoma (FUS) exists in two forms, a free monomer and in assemblies (stacked β-sheet structures). The repeated [S/G]Y[S/G] motifs are modeled as oriented in such a way that the tyrosines are stacked between the β-sheets forming π-stacking interactions that stabilize the polymeric structure. As FUS shifts from the monomer state to the assembled state, tyrosines become occluded. The present invention can be used to detect such a shift of FUS to the assembled state.

As another example, the present invention also features detecting a relative level of protein in two different folded states. For example, first, FUS, MBP, and BSA in their folded states may be subjected to conditions for labeling (e.g., fluorescent labeling) their free tyrosines. The proteins may then be denatured (e.g., in 1% SDS) and again be subjected to the conditions for labeling free tyrosines. The tyrosines previously occluded in the folded state may then be observed by an increase in fluorescent labeling. In other examples, proteins can be labeled at various reactive side chains, including but not limited to amines, carboxyls, phenols, and thiols. In some embodiments, proteins may be digested to increase sensitivity of detecting a unique pattern of selective labeling through standard techniques as high resolution SDS-PAGE, MS-MS, and capillary zone electrophoresis followed by laser induced fluorescence (CZE-LIF).

Note that hydrogen-deuterium exchange (H-D exchange) is a method that has previously been used to attempt to elucidate the tertiary structure of a molecule (e.g., protein). When the solvent comprises $D_2O$, deuterons become incorporated into the protein depending on the accessibility of the hydrogens of the molecule (e.g., the amid hydrogens of the backbone of the protein). However, H-D exchange is challenging because it generally requires NMR spectroscopy and the use of $D_2O$. The methods and systems of the present invention provide a faster and cheaper means of evaluating samples for protein aggregation. Further, the present invention features a means of specifically labeling a protein. Fluorescence output may provide simple and direct means of evaluating the extent of labeling of a protein. Also, the present invention allows for the use of multi-well plates and high throughput platforms.

The present invention also features methods for evaluating the pathway to folding of a protein, e.g., by monitoring the molecule as it is subjected to denaturing conditions. The present invention also features methods for evaluating the pathway of a protein shifting from a folded state to an amyloid state.

Proteopathies

The present invention may be used for the detection of (or monitoring of) certain pathological conditions such as proteopathies (protein misfolding diseases), e.g., Alzheimer's disease, Parkinson's disease, Creutzfeldt-Jacob disease, prion disease, amyloidosis, Huntington's disease, frontotemporal lobar degeneration (FTLD), etc. For example, the present invention may be used to detect or monitor particular aggregates or folding states of one or more markers related to Alzheimer's disease.

Amyotrophic Lateral Sclerosis

Many diseases or pathological conditions (e.g., amyotrophic lateral sclerosis (ALS), Alzheimer's disease, etc.) are associated with aberrant protein folding leading to aggregation. Regarding ALS, mutations in most, if not all of the genes that are known to lead to ALS result in protein aggregation. One such gene is FUS (fused in sarcoma). Inventors have discovered that insoluble aggregates of FUS form in fibroblast cells, which is not found in wild-type controls. For example, the majority of FUS protein in normal cells is in small complexes, but between 60 to nearly 100% of FUS is trapped in aggregates in ALS patient cells.

Often nuclear aggregates in many tissues cannot be observed by histological methods. FUS neuronal cytoplasmic inclusions (NCIs) have been observed in sporadic and non-SOD1 familial ALS patients by two independent studies. A histological study of skin biopsies showed a marked accumulation of FUS in keratinocytes with all tested sporadic ALS cases. However, two labs (including that of Inventors) did not find this in cultured fibroblasts of ALS patients. While histological analysis of skin biopsies has not been criticized for specificity, studies have shown them to suffer from low sensitivity and therefore reduced reliability in diagnosing neurodegenerative disease. TDP-43 is found in NCIs in more than 90% of ALS patients. Inclusions have also been noted in cultured fibroblasts and tissue-engineered skins. The present invention may be used for the detection of (or monitoring of) certain pathological conditions such as amyotrophic lateral sclerosis (ALS). For example, the present invention may be used to detect or monitor particular aggregates or folding states of one or more markers related to ALS.

SUMMARY OF THE INVENTION

The present invention features methods for detecting the presence of occluded amino acids in a protein of interest in a test sample. In some embodiments, the method comprises subjecting the test sample to a reaction adapted to covalently modify label-able amino acids (e.g., tyrosines) with a first reactive moiety conjugated to a first detectable label; subjecting the sample to denaturing conditions; subjecting the test sample to a reaction adapted to covalently modify label-able amino acids (e.g., tyrosines) with a first reactive moiety conjugated to a second detectable label or a second reactive moiety conjugated to a second detectable label, wherein the first detectable label and second detectable label are visually distinct; and making visible the first detectable label and second detectable label. The presence of the second detectable label in addition to the first detectable label may be indicative of the presence of occluded amino acids (e.g., tyrosines) in the protein of interest in the test sample. The presence of the second detectable label in addition to the first detectable label may be indicative of the protein of interest in the test sample in an aggregate form.

In some embodiments, the protein of interest is a biomarker associated with amyotrophic lateral sclerosis (ALS). In some embodiments, the protein of interest is a biomarker associated with a proteopathy. In some embodiments, the proteopathy is Alzheimer's disease, Parkinson's disease, Creutzfeldt-Jacob disease, prion disease, an amyloidosis, Huntington's disease, frontotemporal lobar degeneration (FTLD), type 2 diabetes, a cancer associated with p53 aggregation, amyotrophic lateral sclerosis (ALS), chronic traumatic encephalopathy, dementia, tauopathies, retinal ganglion cell degeneration, cerebral beta amyloid angiopathy, Alexander disease, cerebral hemorrhage with amyloidosis, CADASIL, seipinopathies, familial amyloidotic neuropathy, senile systemic amyloidosis, cataracts, medullary thyroid carcinoma, pituitary prolactinoma, cystic fibrosis, sickle cell disease, or pulmonary alveolar proteinosis. In some embodiments, the presence of occluded amino acids in the protein of interest in the test sample is associated with the presence of ALS. In some embodiments, the presence of the protein of interest in aggregate form in the test sample is associated with the presence of ALS.

The present invention also features methods of detecting ALS amyotrophic lateral sclerosis (ALS). The method may be as described above, wherein the presence of the second detectable label in addition to the first detectable label may be indicative of the protein of interest in an aggregate form, which may be indicative of the presence of ALS In some embodiments, the label-able amino acid comprises tyrosine, arginine, lysine, glutamate, aspartate, cysteine, or a combination thereof. In some embodiments, the protein of interest is selected from fused in sarcoma (FUS), TDP-43, hnRNPA1, GRN, SQSTM1, SOD1, PFN1, VCP, OPTN, SETX, ANG, hnRNPA2B1, UBQLN2, APP, Tau, APPBP2, APCS, APBA2, PSEN1, PSEN2, HTT, Alpha-synuclein, NEFL light chain, NEFL medium chain, p53, IAPP, insulin, B2M, PrP, or a combination thereof. In some embodiments, the reactive moiety comprises diazirine, maleimide, NHS ester, dansyl chloride, acetyl azide, isothiocyanate, bimane amine, trifluoromethanesulfonate, aryl azides, or a combination thereof. In some embodiments, the reactive moiety comprises diazirine, maleimide, NHS ester, dansyl chloride, acetyl azide, isothiocyanate, bimane amine, trifluoromethanesulfonate, aryl azides, or a combination thereof. In some embodiments, the detectable label comprises coumarin, fluorophores, radiolabels, heavy isotopes, metal chelators, biotin, peptides, fluorescent microspheres, fluorescent proteins, quantum dots, or a combination thereof. In some embodiments, occluded amino acids are associated with a protein in a bound state, a folded state, or an interactive state wherein the protein interacts with a second molecule (e.g., a protein, an RNA molecule, a DNA molecule, or a combination thereof). In some embodiments, making visible the detectable label comprises subjecting the sample to fluorescence spectroscopy or imaging, NMR, chromatography, electrophoresis, affinity purification, immunopurification, MRI, or a combination thereof. In some embodiments, denaturing conditions comprises a detergent, heat, urea, or a combination thereof. In some embodiments, the method further comprises digesting the protein of interest.

The present invention also features methods of detecting proteopathies. The method may comprise subjecting a test sample from a patient suspected of having a proteopathy to a reaction adapted to covalently modify label-able amino acids with a first reactive moiety conjugated to a first detectable label; subjecting the test sample to denaturing conditions; subjecting the test sample to a reaction adapted to covalently modify label-able amino acids with a first reactive moiety conjugated to a second detectable label or a second reactive moiety conjugated to a second detectable label, wherein the first detectable label and second detectable label are visually distinct; and making visible the first detectable label and second detectable label. The presence of the second detectable label in addition to the first detectable label may be indicative of the protein of interest in an aggregate form, which is indicative of the presence of the proteopathy.

The present invention also features methods for detecting Alzheimer's disease using methods as described herein. For example, the method may comprise subjecting a test sample from a patient suspected of having Alzheimer's disease to a reaction adapted to covalently modify label-able amino acids of a protein of interest associated with Alzheimer's disease with a first reactive moiety conjugated to a first detectable label, the protein of interest being selected from APP, Tau, APPBP2, APCS, APBA2, PSEN1, and PSEN2; subjecting the test sample to denaturing conditions; subjecting the test sample to a reaction adapted to covalently modify label-able amino acids with a first reactive moiety conjugated to a second detectable label or a second reactive moiety conjugated to a second detectable label, wherein the first detectable label and second detectable label are visually distinct; and making visible via fluorescence spectroscopy or imaging the first detectable label and second detectable label. The presence of the second detectable label in addition to the first detectable label may be indicative of the protein of interest in an aggregate form, which may be indicative of the presence of Alzheimer's disease. In some embodiments, the method is for detecting Huntington's disease. In some embodiments, the protein of interest comprises HTT. The presence of the second detectable label in addition to the first detectable label may be indicative of the protein of interest in an aggregate form, which may be indicative of the presence of Huntington's disease. In some embodiments, the method is for detecting Parkinson's disease. In some embodiments, the protein of interest comprises Alpha-synuclein, NEFL light chain, and NEFL medium chain. The presence of the second detectable label in addition to the first detectable label may be indicative of the protein of interest in an aggregate form, which may be indicative of the presence of Parkinson's disease. In some embodiments, the method is for detecting Creutzfeldt-Jakob disease. In some embodiments, the protein of interest comprises PrP. The presence of the second detectable label in addition to the first detectable label may be indicative of the protein of interest in an aggregate form, which may be indicative of the presence of Creutzfeldt-Jakob disease.

In some embodiments, the method further comprises digesting the protein of interest.

The present invention also features kits for detecting the presence of a protein of interest in aggregate form in a test sample. In some embodiments, the kit comprises a first reactive moiety conjugated to a first detectable label, the first reactive moiety is adapted to covalently modify label-able amino acids on the protein of interest, and a second reactive moiety conjugated to a second detectable label, the second reactive moiety is adapted to covalently modify label-able amino acids on the protein of interest, the detectable labels are adapted to be quantitated. In some embodiments, the kit comprises a control sample.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 1 shows labeling of folded BSA and heat-denatured BSA. BSA was labeled (lysines, N-terminus), protein was immobilized, and fluorescence read on a microplate reader.

FIG. 2A and FIG. 2B show FUS and MBP denatured by detergent (SDS) and/or heat (95° C.) and then labeled with TBP-C. Fluorescence for SDS-PAGE resolved proteins was measured at 488 nm and total protein was measured by coommassie staining. FIG. 2B shows additional experiments comparing labeling of MBP in PBS and MBP denatured by detergent (SDS) and/or heat.

FIG. 3 shows MBP (pdb: 1ANF) in a folded state. Some of the exposed and buried/folded tyrosines are noted. Some residues are available for chemical labeling in this folded state. Upon denaturing the protein, additional residues would be available for labeling.

FIG. 4 shows a schematic of a folded protein and an aggregate/amyloid protein. In the folded protein (top left), solvent exposed peptides are available for labeling, but the total protein remains resistant to trypsin digestion (bottom left). Aggregates of a denatured protein are more susceptible to digestion but amyloids protect more of the protein from labeling (right top and bottom).

FIG. 6 shows that few tyrosines in BSA are solvent exposed in the folded state. BSA (pdb: 4OR0) contains many tyrosines (top panels) that are buried and some that are solvent exposed. The surface models (bottom panels) of BSA conceal the buried tyrosines, revealing that they do not have access to the solvent.

FIG. 7 shows total cellular protein can be labeled in cell lysate. Addition of TBD-conjugated to coumarin (TBD-C) labels proteins in total cell lysate. As a positive control, purified FUS and MBP are also labeled in solution. In the absence of TBD-C, no 488 nm fluorescence is detected.

This involves amino acid residues capable of labeling including tyrosines, arginines, and glutamates (highlighted blue).

Figure 14A:
Figure 14B:
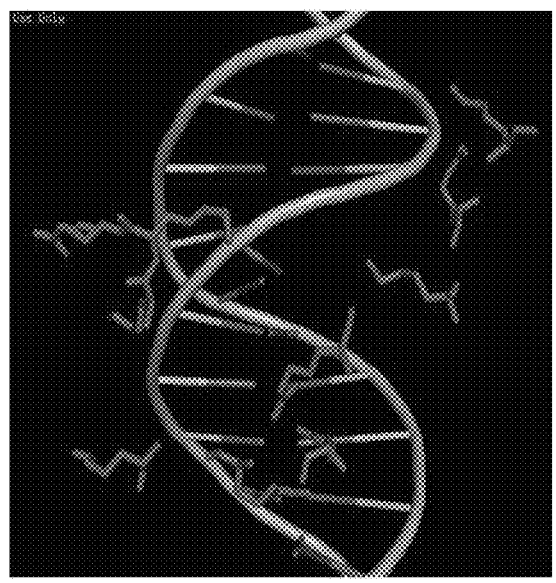

FIG. 14A and FIG. 14B shows the protein p65 (green) has specific residues occluded by a DNA molecule (pdb: 1RAM) (left). This involves amino acid residues capable of labeling including arginines and lysines (highlighted red right).

Figure 15:
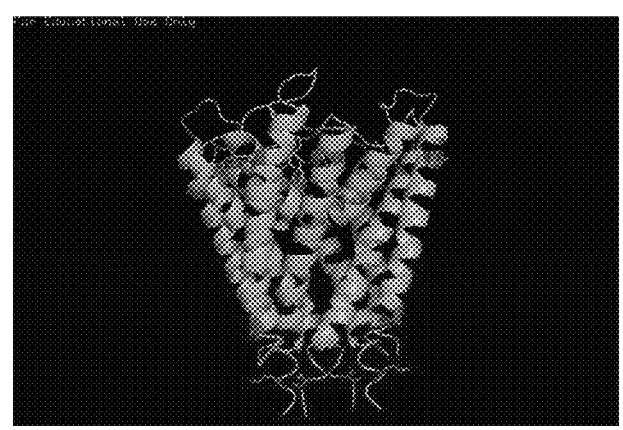

FIG. 15 shows the potassium channel has specific residues occluded by the lipid interactions (pdb: 1BL8). This involves amino acid residues capable of labeling including arginines and tyrosines (highlighted blue). Changes in amino acid labeling due to lipid interactions can be potentiated by treatments with detergents, electrical voltage, or electrophysiological stimulation.

Figure 16:
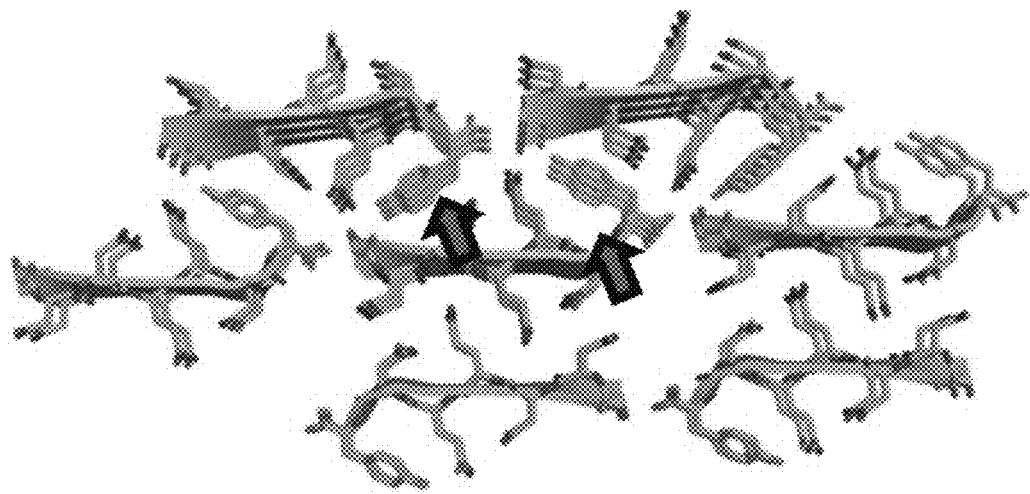

FIG. 16 shows sup35 yeast prion (pdb: 2OMP) with tyrosines (red arrows) occluded from chemical labeling in the aggregate form.

Figure 17:
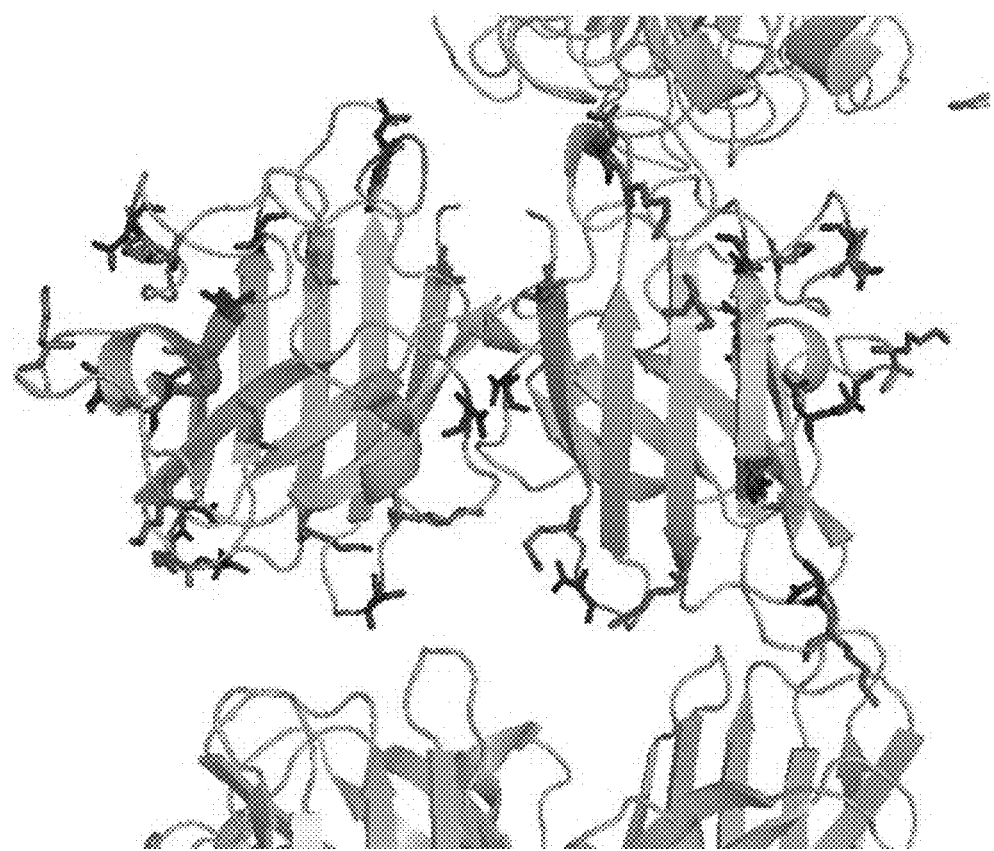

FIG. 17 shows SOD1 (pdb: 1UXM) with an A4V mutation forms aggregates with lysines (pink) and aspartates (blue) either solvent exposed or occluded from chemical labeling in the aggregate state.

Figure 18:
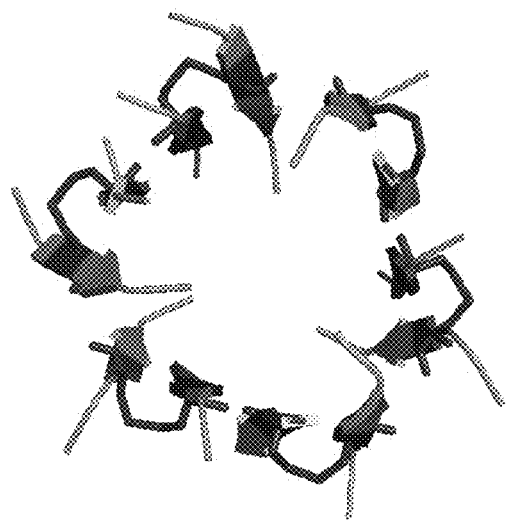

FIG. 18 shows human prion protein (pdb: 4E1I) forms amyloids with exposed cysteines (blue) available for chemical labeling.

Figure 19:
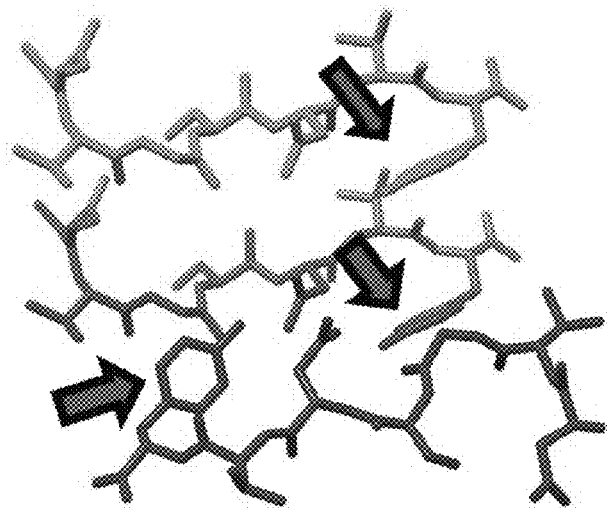

FIG. 19 shows islet amyloid polypeptide (IAPP, pdb: 3FTK) with tyrosines (red arrows) occluded from chemical labeling in the aggregate form.

Figure 20:
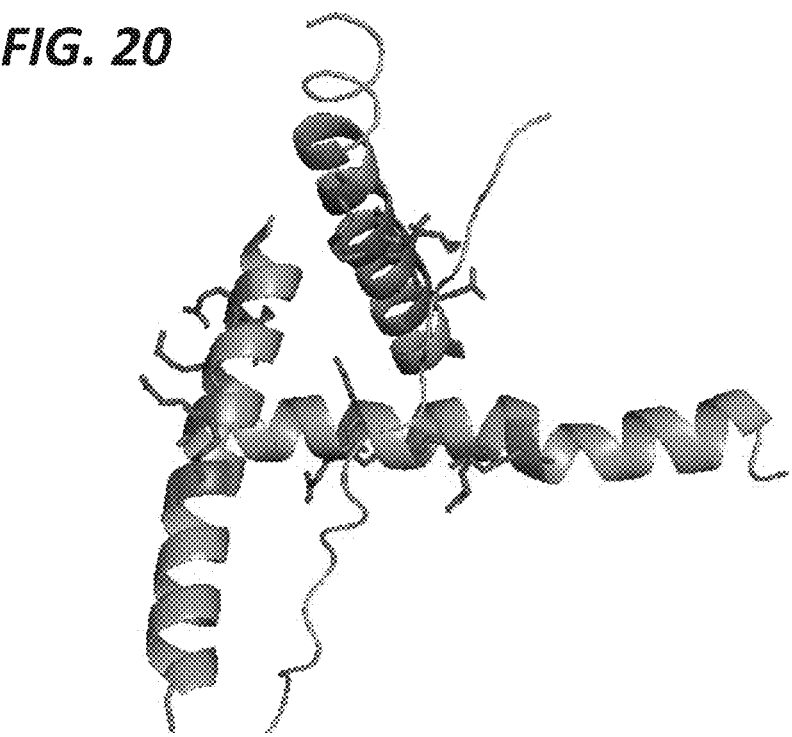

FIG. 20 shows the N-terminal amino acids up to the poly-Q region (pdb: 3IO4) with lysines and glutamates (red) able to be chemically labeled to detect occlusion induced by expansion repeat associated aggregates.

Figure 21:
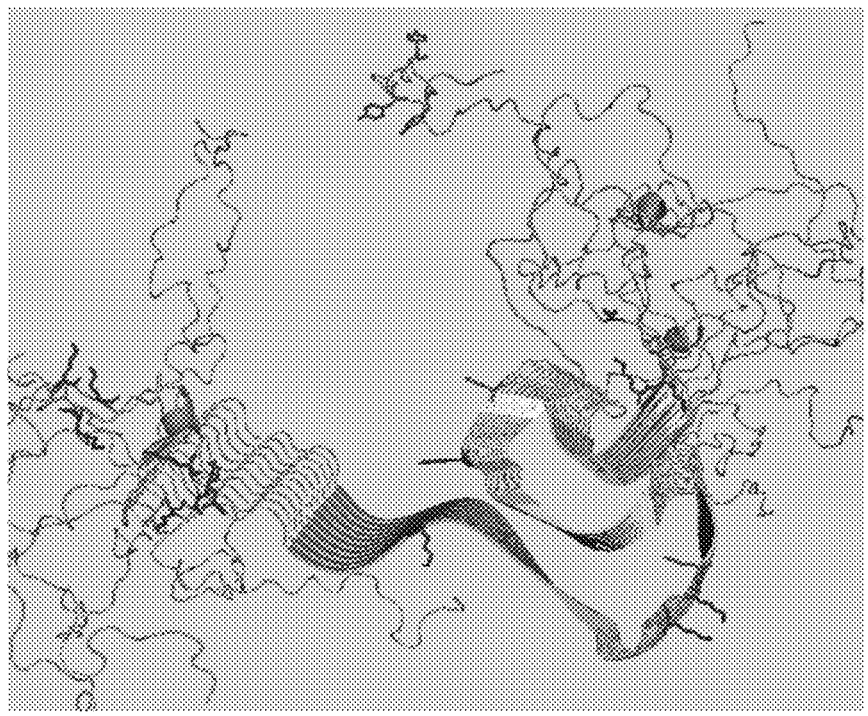

FIG. 21 shows alpha synuclein (pdb: 2N0A) with tyrosines and glutamates (red) and lysines (blue) able to become occluded from chemical labeling in the aggregate form.

Figure 22:
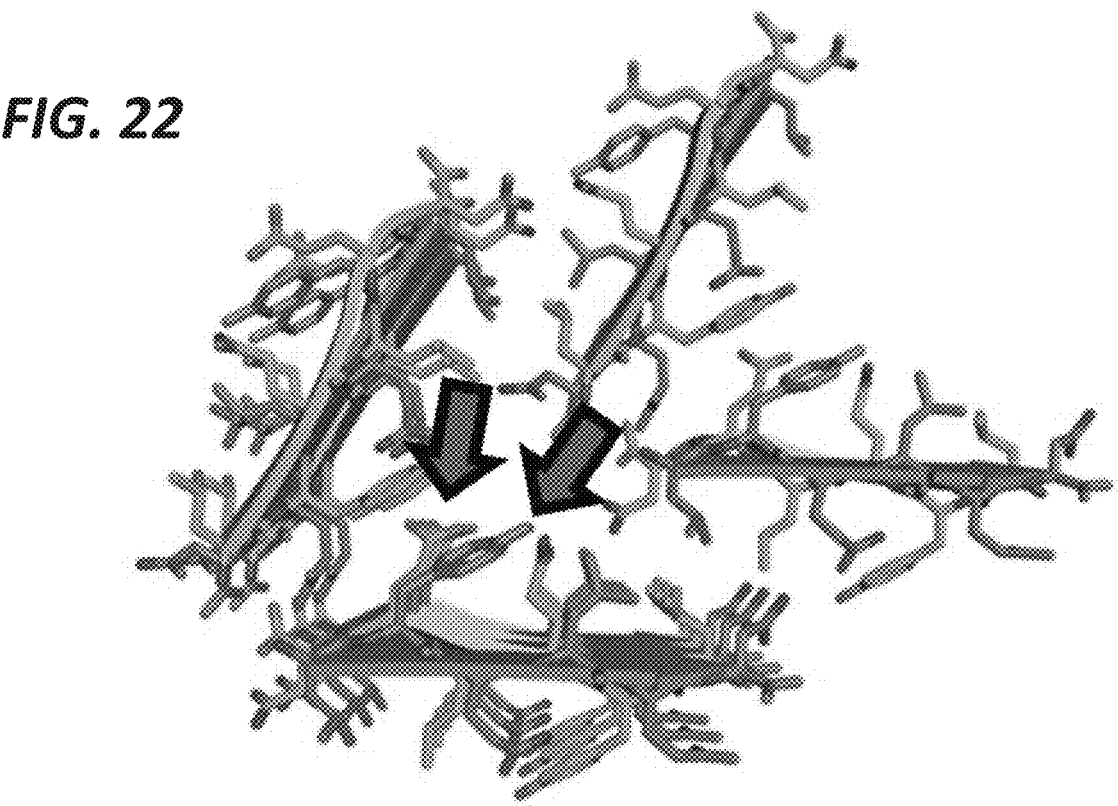

FIG. 22 shows human insulin amyloids (pdb: 2OMP) with tyrosines and glutamates (red arrows) occluded from chemical labeling in the aggregate form.

DETAILED DESCRIPTION OF THE INVENTION

The present invention features methods, systems, and compositions for detecting molecules in an aggregate state, a bound or unbound state, a folded, unfolded, or misfolded state, an interactive or non-interactive states, etc. The present invention also features methods, systems, and compositions for detecting or monitoring proteopathies, e.g., methods, systems, and compositions for detecting protein aggregation (or other folding state or interactive state) related to a pathological condition, e.g., pathological condition associated with protein misfolding (proteopathies). Proteopathies may include but are not limited to Alzheimer's disease, Parkinson's disease, Creutzfeldt-Jacob disease, prion disease, amyloidosis (e.g., insulin amyloidosis, kidney dialysis amyloidosis, senile amyloidosis, AL amyloidosis, AH amyloidosis, AA amyloidosis, aortic medial amyloidosis, lysozyme amyloidosis, fibrinogen amyloidosis, cardiac atrial amyloidosis, etc.), Huntington's disease, frontotemporal lobar degeneration (FTLD), type 2 diabetes, certain cancers (e.g., p53 aggregation related cancers, etc.), amyotrophic lateral sclerosis (ALS), chronic traumatic encephalopathy, dementia, tauopathies, retinal ganglion cell degeneration, cerebral beta amyloid angiopathy, Alexander disease, cerebral hemorrhage with amyloidosis, CADASIL, seipinopathies, familial amyloidotic neuropathy, senile systemic amyloidosis, cataracts, medullary thyroid carcinoma, pituitary prolactinoma, cystic fibrosis, sickle cell disease, pulmonary alveolar proteinosis, the like, etc.

The present invention also features methods, systems, and compositions for detecting amyotrophic lateral sclerosis (ALS) or for monitoring ALS.

Generally, the methods of the present invention allow for detecting molecules in an aggregate state, a bound or unbound state, a folded, unfolded, or misfolded state, an interactive or non-interactive states, etc.

The present invention also features comparing or evaluating changes in states of said molecules, e.g., changes in protein folding conformations (e.g., shift to an assembled state), changes in aggregation. The present invention also features detecting a relative level of protein in two different folded states. The present invention also features methods for evaluating the pathway to folding of a protein, e.g., by monitoring the molecule as it is subjected to denaturing conditions.

The methods of the present invention feature evaluating an amount of labeling of a test molecule (e.g., protein) and comparing that amount of labeling to an amount of labeling of a control (the control may be a denatured version of the molecule, e.g., protein, a sample of the protein of interest in a non-aggregate form, in the free state, purified, etc.). Comparing the amount of labeling of the test sample of the control sample may help determine whether the protein is folded, unfolded, misfolded, in aggregate or non-aggregate form, is interacting with another molecule (or not), etc. Without wishing to limit the present invention to any theory or mechanism, it is believed that certain residues within a protein in a more folded or aggregated state (or interactive state) may be occluded, whereas in the free state or unfolded or misfolded state, those residues would be exposed. If exposed in the free state, the residues may be able to be labeled. However, if the residues were occluded, they would not be able to be labeled. Without wishing to limit the present invention to any theory or mechanism, it is believed that in addition to occlusion due to folding, aggregation, binding, or interaction, chemical or electrostatic environment may also limit labeling of a protein of interest. Thus, the present invention may be used to distinguish (or monitor, etc.) the chemical or electrostatic environment of a particular amino acid, region, or peptide.

In some embodiments, the present invention may help detect the presence of a mutant protein, e.g., a misfolded protein that may affect the folding of the wild type version that is near or within a range of being affected by the misfolded/mutant protein.

As a non-limiting example, the methods may comprise labeling a protein of interest in a test sample (e.g., a tissue sample, e.g., a skin biopsy, etc.) with a first label (a detectable label). (Note that residues of a target protein may be prevented from labeling due to occlusion if the target protein is in a folded state, an interactive state, an aggregate form, etc.; if not, the target protein would likely be labeled in an amount similar to that of the control wherein the target protein is denatured, non-aggregated, non-interactive, unfolded, etc.). In some embodiments, the protein in the sample is then purified (e.g., under denaturing conditions). In some embodiments, the amount of labeling is compared (and quantitated) between equal amounts of the target protein in a control and the target protein from the test sample.

In some embodiments, a control is not performed alongside the test. In some embodiments, the amount of labeling in the test sample is compared to a particular threshold associated with a control state (e.g., there may be established ranges of labeling that will be indicative of a folded or non-folded state, an aggregate or non-aggregate state, a misfolded state, a bound state, an unbound state, an interactive state, a non-interactive state). A biological control may include a different cell type, different tissue, a non-diseased sample, or another organism.

The present invention is not limited to the aforementioned methods. For example, the methods of the present invention may be performed in a single tube or well. A target molecule (e.g., molecule of interest), e.g., a protein, nucleic acid, etc., is labeled. For example, an amino acid residue of a protein is labeled. In some embodiments, the amino acid (of the protein of interest) to be labeled includes but is not limited to tyrosine, arginine, lysine, glutamate, aspartate, cysteine, or a combination thereof.

In some embodiments, the modification of a molecule (e.g. an amino acid or other appropriate molecule) is catalyzed by enzymatic activity. For example, the enzyme transglutaminase can catalyze the labeling of lysine conjugated labels to glutamine. For example, the enzyme ubiquitin ligase can transfer a labeled ubiquitin molecule to a free lysine residue. For example, enzymes responsible for N-linked and O-linked glycosylation can transfer labeled glycans to asparagines, serines, threonines, or lipids.

Any appropriate labeling chemistry may be considered. In some embodiments, PTAD chemistry is used for labeling the amino acid of interest. In some embodiments, modification of the amino acid comprises using reactive moieties including but not limited to diazirine, maleimide, NHS ester, dansyl chloride, acetyl azide, isothiocyanate, bimane amine, trifluoromethanesulfonate, aryl azides, etc.). In some embodiments, the reactive moieties are conjugated to a detectable label. Detectable labels are well known to one of ordinary skill in the art. For example, the detectable label may comprise fluorophores, radiolabels, heavy isotopes, metal chelators, biotin, peptides, or the like. The present invention is not limited to the aforementioned reactive moieties and detectable labels.

In some embodiments, making visible the detectable label comprises subjecting the sample to fluorescence imaging. In some embodiments, making visible the detectable label comprises subjecting the sample to electrophoresis (e.g., SDS-PAGE). In some embodiments, making visible the detectable label comprises subjecting the sample to chromatography. In some embodiments, making visible the detectable label comprises subjecting the sample to fluorescence spectroscopy or imaging. In some embodiments, making visible the detectable label comprises subjecting the sample to NMR. In some embodiments, making visible the detectable label comprises subjecting the sample to MRI. In some embodiments, making visible the detectable label comprises subjecting the sample to radio imaging. In some embodiments, making visible the detectable label comprises subjecting the sample to mass spectrometry. In some embodiments, making visible the detectable label comprises subjecting the sample to streptavidin-modified nanoparticles. In some embodiments, making visible the detectable label comprises subjecting the sample to enzymes, antibodies, the like, or a combination thereof. An example for fluorescence detection includes immobilizing the molecule of interest to a solid substrate (nitrocellulose, PVDF, plastic dish or multi-well plate, glass microscope slide or multi-well plate, etc.) and visualizing by fluorescence imaging.

In some embodiments, the protein (e.g., target protein) is not purified from the sample. For example, in some embodiments, the target protein is in such high abundance that purification from other cellular proteins is not necessary (e.g., hemoglobin in red blood cells). Methods of purifying proteins are well known to one of ordinary skill in the art. In some embodiments, labeled biomolecule (e.g., the target protein, nucleic acid, peptide, etc.) is purified using beads conjugated with a target-specific antibody or tagged affinity interactor. In some embodiments, the target protein is purified using beads conjugated with a binding partner of the target protein. The present invention is not limited to the aforementioned methods or reagents. For example, total cellular or tissue-derived biomolecules that have been labeled (e.g. proteins, nucleic acids, peptides, etc.) can be purified and subjected to massive parallel detection such (e.g. mass spectrometry, targeted mass spectrometry, bottom up and top down mass spectrometry, etc.). The present invention is not limited to the aforementioned methods or reagents.

Non-limiting examples of different mechanisms for conjugating the chemical label or "marker" include but are not limited to (1) direct ligation, (2) conjugating markers to modified amino acids incorporated into protein synthesis, (3) enzymatic labeling with enzymes such as transglutaminase, or (4) affinity labeling based on strong binding interactions such as that between biotin and avidin. In (1), examples are like those described above involving a reactive group (e.g. diazerine, PTAD, NHS, maleimide, etc.) chemically conjugated to the marker. In (2), an example would be to culture a biological sample in the presence of modified amino acids that will be incorporated into protein synthesis. After incorporation of these modified amino acids, they will be subsequently be targeted by labeling with a label or marker as described herein. In (3), the example mentioned is using transglutaminase to crosslink glutamine residues to substrates conjugated to a label or marker. In (4), the example mentioned is directly labeling amino acid residues with a reactive group conjugated to an affinity label such as biotin. Then the label or marker will be conjugated to a binding factor, which in this example would be biotin. After amino acids are labeled with the affinity label, the binder conjugated to the label or marker will be added to make the labeling detectable. In this example, the label or marker would be conjugated to avidin.

In some embodiments, the sample comprises tissue, bodily fluid, or any other appropriate sample. For example, in some embodiments, the sample comprises blood or portions of blood, skin, eye tissue, brain tissue or CNS fluids, etc. In some embodiments, the methods of the present invention are performed with patient-derived cells, e.g., fibroblasts, CNS cells, etc.

In some embodiments, the dynamic range of detection may be amplified by techniques including but not limited to increasing the bulkiness of the chemical label/marker conjugate, targeting more rare or specific amino acids, comparing signal to control samples denatured by standard techniques including heat, urea, guanidinium, or organic solvents, preceding detection with a biochemical purification step such as Size Exclusion Chromatography (SEC), or digesting the protein of interest into peptides and detecting specific labeled peptides by standard techniques including high-resolution SDS-PAGE, HPLC, paper lithography, 2D electrophoresis, or mass spectrometry. Some disease aggregates in diseases such as neurodegenerative diseases may be resistant to falling apart by treatment with denaturing conditions (e.g., FUS and TDP-43 in ALS; prions and amyloids in Alzheimer's, etc.).

In some embodiments, the methods of the present invention could be performed in fluid phase. In some embodiments, the present invention could be used to detect platelet aggregation. In some embodiments, the present invention is used for monitoring thrombosis.

In some embodiments, the present invention features the use of labels that only fluoresce or become detectable (as described herein) if bound to the protein of interest.

As previously discussed, the present invention features methods for detecting or evaluating protein conformations, such as an aggregate state. In some embodiments, the method comprises labeling a portion of a test sample (e.g., via various labeling methods such as but not limited to diazonium chemistry as described below, or NHS ester chemistry, pyridyldithiol chemistry, PTAD, maleimide chemistry, epoxide chemistry, fluorobenzene chemistry, EDC chemistry, and diazirine chemistry, etc.). The method may further comprise labeling a portion of the test sample wherein that portion of the test sample has been denatured via a denaturing agent. The method may further comprise comparing the amount of labeling in the two test samples. The level of labeling may help elucidate the conformation of the protein in the test sample. For example, the level of labeling of the denatured sample compared to the non-denatured sample may help determine that the protein in the test sample is in an aggregate form. In some embodiments, the level of labeling of the denatured sample compared to the non-denatured sample may help determine that the protein in the test sample is in a naturally folded state as opposed to a different conformation (e.g., an aggregate form, etc.). In some embodiments, the method further comprises comparing the amount of labeling in the denatured sample and/or the non-denatured sample to labeling of one or more control samples.

In some embodiments, labeling occurs via diazonium chemistry (e.g., fluorescent-conjugated aryl diazonium). For example, in some embodiments, a detectable label is conjugated to or is part of a triazabutadiene molecule. The triazabutadiene may be added to the sample and activated (e.g., via an acid or other trigger) to yield a diazonium species. A diazonium species in close proximity to a tyrosine residue will react to form an azobenzene bond joining the diazonium and the tyrosine. Thus, the tyrosine residues of a sample may be labeled via diazonium chemistry. The present invention is not limited to labeling via diazonium chemistry. Other methods of labeling are known to one of ordinary skill in the art. Further, the present invention is not limited to labeling of tyrosine. In some embodiments, the amino acid (of the protein of interest) to be labeled includes but is not limited to tyrosine, arginine, lysine, glutamate, aspartate, cysteine, or a combination thereof.

Denaturing agents are known to one of ordinary skill in the art. In some embodiments, the denaturing agent comprises SDS, urea, heat, etc.

Detectable labels are well known to one of ordinary skill in the art. For example, the detectable label may comprise fluorophores, radiolabels, heavy isotopes, metal chelators, biotin, peptides, fluorescent microspheres, fluorescent proteins, quantum dots, or the like. The present invention is not limited to the aforementioned reactive moieties and detectable labels.

Without wishing to limit the present invention to any theory or mechanism, it is believed that the present invention shows that increased labeling of proteins can occur when the proteins are in an unfolded state and that one can differentially label a protein based on which residues (and how many of those residues) are exposed on a surface. In some embodiments, the amount of protein in each conformational state, whether in isolated solutions or in cells and whether these states are folded and unfolded or monomer and polymer, may be quantified by the difference in labeling observed between that of the protein fully in one state and that fully in the other state. Thus, in some embodiments, a shift in the dynamic equilibrium can be inferred by a shift in the amount of labeling towards that of one state or the other.

As previously discussed, the present invention also features methods, systems, and compositions for detecting protein aggregation or protein binding. For example, methods of the present invention may feature comparing the amount of labeling of a protein of interest in a test sample (e.g., a sample being tested for the presence of the protein of interest in aggregate form) with a control sample (e.g., a sample comprising the protein of interest in a non-aggregate form, e.g., free state, e.g., purified protein). In some embodiments, the method comprises subjecting the protein of interest in the sample (e.g., test sample, control sample) to a reaction adapted to covalently modify and label one or more amino acids of the protein of interest. The method further comprises making visible the detectable labels on the protein of interest in the samples. In some embodiments, if less labeling is present in the test sample as compared to the control sample, the test sample comprises the protein of interest in aggregate form. In some embodiments, if labeling is the same (or about the same) in the test sample as compared to the control sample, the test sample does not comprise the protein of interest in aggregate form.

Without wishing to limit the present invention to any theory or mechanism, it is believed that the methods of the present invention have good sensitivity because the methods may feature labeling, then lysing of cells, and then immunopurification of the protein (e.g., FUS, TPD-43, etc.) from cells. In some embodiments, the immunopurification assays provide enough protein to visualize by silver or coomassie staining. Also, unlike tissue histology, the immunopurification protocol may have no detectible background, meaning that sensitivity is only limited by the intensity of the label.

As previously discussed, the present invention also features methods, systems, and compositions for detecting interactions involving biomolecules, e.g., detecting a bound or interactive state of a molecule of interest. Molecules of interest may include but are not limited to oligonucleotides, proteins, modified oligonucleotides (e.g., locked nucleic acids, phophorothioate oligonucleotides, 2' O-methyl oligonucleotides, biotinylated nucleotides, etc.), or any other appropriate molecule (e.g., a SOMAmer®, etc.), or combinations thereof. Table 1 describes various non-limiting examples of interacting molecules that may interact with the molecule of interest:

TABLE 1

| Molecule of Interest | Interacting Molecule |
|---|---|
| Protein | Protein |
| DNA | Protein |
| RNA | Protein |
| Modified Oligo | Protein |
| Lipid | Protein |
| SOMAmer | Protein |
| Protein | DNA |
| DNA | DNA |
| RNA | DNA |
| Modified Oligo | DNA |
| Lipid | DNA |
| SOMAmer | DNA |
| Protein | RNA |
| DNA | RNA |
| RNA | RNA |
| Modified Oligo | RNA |

TABLE 1-continued

| Molecule of Interest | Interacting Molecule |
|---|---|
| Lipid | RNA |
| SOMAmer | RNA |
| Protein | SOMAmer |
| DNA | SOMAmer |
| RNA | SOMAmer |
| Modified Oligo | SOMAmer |
| Lipid | SOMAmer |
| SOMAmer | SOMAmer |
| Protein | Lipid |
| DNA | Lipid |
| RNA | Lipid |
| Modified Oligo | Lipid |
| Lipid | Lipid |
| SOMAmer | Lipid |
| Protein | Small Molecule |
| DNA | Small Molecule |
| RNA | Small Molecule |
| Modified Oligo | Small Molecule |
| Lipid | Small Molecule |
| Small Molecule | Protein |
| Small Molecule | DNA |
| Small Molecule | RNA |
| Small Molecule | Lipid |
| Small Molecule | Modified Oligo |

Without wishing to limit the present invention to any theory or mechanism, it is believed that certain areas of a molecule of interest may be occluded in some situations (e.g., in a bound or interactive state) whereas in other situations (e.g., unbound, non-interactive state) those areas may be exposed: if exposed, the areas may be able to be labeled, whereas if the areas were occluded, they would not be able to be labeled. As an example, an aggregated form of a protein is likely to be labeled less than the protein in a non-aggregated form. The present invention is not limited to protein-protein interactions. The present invention is not limited to detecting aggregated states of proteins. In some embodiments, the molecule features a pharmacological small molecule binder (e.g. inhibitor, antagonist, activator, etc.).

In some embodiments, the methods or systems of the present invention feature comparing the amount of labeling or modification of a molecule of interest with the amount of labeling or modification of the molecule in a control. In some embodiments, the method comprises subjecting the molecule of interest in a sample (e.g., test sample, control sample, both, etc.) to a reaction adapted to modify and/or label one or more areas or residues (e.g., amino acids, nucleotides, etc.) of the molecule of interest. The method may further comprise making visible the detectable labels or modifications on the molecule of interest. In some embodiments, if less labeling is present in the test sample as compared to the control sample, the test sample comprises the molecule of interest in a bound or interactive form. In some embodiments, if less labeling is present in the test sample as compared to the control sample, the test sample comprises the molecule of interest in a an assembled form. In some embodiments, if less labeling is present in the test sample as compared to the control sample, the test sample comprises the molecule of interest in an aggregate form. In some embodiments, if labeling is the same (or about the same) in the test sample as compared to the control sample, the test sample does not comprise the molecule of interest in bound or interactive form or the test sample comprises the molecule of interest in a less bound or less interactive form. In some embodiments, if labeling is the same (or about the same) in the test sample as compared to the control sample, the test sample does not comprise the molecule of interest in bound or interactive form or the test sample comprises the molecule of interest in a less assembled form or aggregate form.

The bound or interactive form or assembled or aggregate form may refer to interactions with various other types of molecules. For example, in some embodiments, the molecule of interest is protein, DNA, or RNA, a chemically modified oligonucleotide, etc., and the molecule of interest may be interacting with protein, DNA, or RNA, a chemically modified nucleotide, etc. (see Table 1 above for non-limiting examples of combinations of molecules binding or interacting or aggregating or assembling, etc.). In some embodiments, the interacting molecule may comprise protein, peptide, nucleic acid, oligonucleotide, biological substrate, or pharmacological agent, the like, or a combination thereof. Detection of the labeled molecule of interest includes fluorescence, mass spectrometry, nuclear magnetic resonance, etc.

In some embodiments, the portion of the molecule of interest that is labeled or modified is a nucleotide. In some embodiments, portion of the molecule that is labeled or modified is an amino acid. Examples of amino acids that may be labeled include but are not limited to tyrosine, arginine, lysine, glutamate, aspartate, proline, serine, threonine, cysteine, or a combination thereof.

Figure 5A:
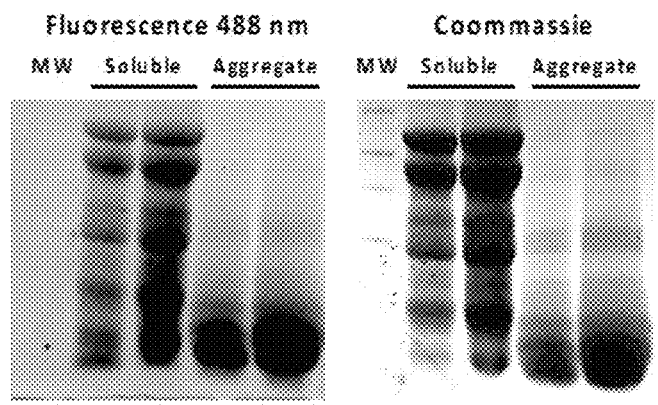
FIG. 5A shows soluble folded BSA is more resistant to digestion by trypsin than aggregate BSA (heat denatured BSA assembles into amyloids but becomes more susceptible to digestion).
Figure 5B:
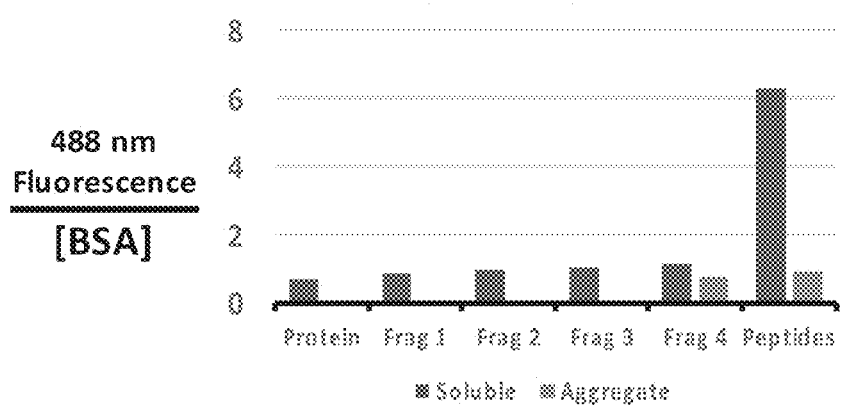
FIG. 5B shows the solvent exposed peptides of the folded BSA protein are highly labeled but peptides of aggregates are less labeled.
Figure 5C:
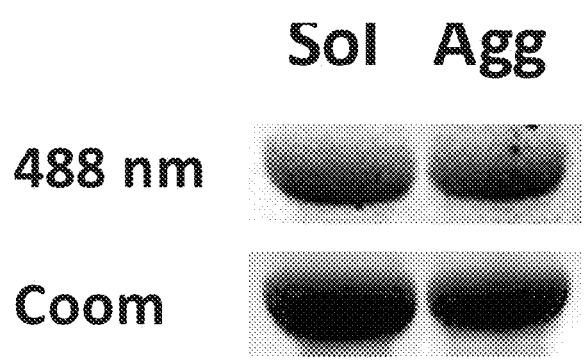
FIG. 5C shows total folded protein is more labeled than aggregate.
Figure 5D:
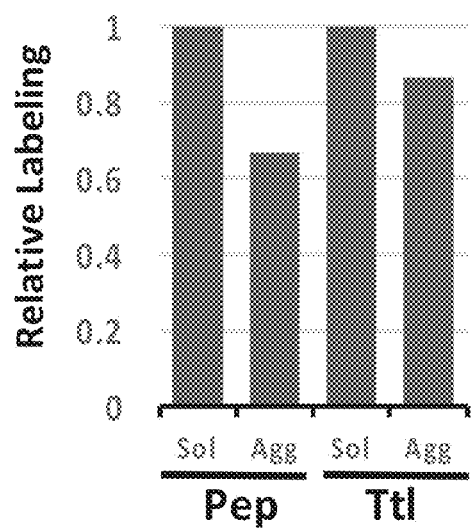
FIG. 5D compares relative labeling of total protein (undigested) in a soluble or aggregate state as well as digested protein in the soluble or aggregate state.

FIG. 1 shows labeling of folded BSA and heat-denatured BSA. 30 or 40 mg of BSA was labeled with fluoraldehyde o-phthaldehyde (OPA), which labels primary amines and some secondary amines, which are found in lysines and the N-terminus and are may be solvent exposed, see dark residues shown in inset). Protein was immobilized in high-binding 96 well plates and fluorescence was read on a POLARstar® Omega microplate reader. FIG. 2A and FIG. 2B show that denatured proteins allow labeling of buried residues to reveal the extent of folding present. Both FUS and MBP were labeled more in their denatured forms. In FIG. 2A, FUS and MBP were denatured by detergent (SDS) and/or heat (95° C.) and then labeled with TBP-C. Fluorescence for SDS-PAGE resolved proteins was measured at 488 nm and total protein was measured by coommassie staining. FIG. 2B shows additional experiments comparing labeling of MBP in PBS and MBP denatured by detergent (SDS) and/or heat. FIG. 3 shows MBP (pdb: 4WMS) in a folded state. Some of the exposed and buried/folded tyrosines are noted. About 8 out of 12 residues are available for chemical labeling in this state. Upon denaturing the protein, about 12 residues would be available for labeling. FIG. 4 shows a schematic of a folded protein and an aggregate/amyloid protein. In the folded protein (top left), solvent exposed peptides are available for labeling, but the total protein remains resistant to trypsin digestion (bottom left). Aggregates of a denatured protein are more susceptible to digestion but amyloids protect more of the protein from labeling (right top and bottom). FIG. 5A, FIG. 5B, FIG. 5C, and FIG. 5D show that digested peptides reveal greater sensitivity when comparing labeling of protein in an aggregate state and folded/soluble. FIG. 5A shows soluble folded BSA is more resistant to digestion by trypsin than aggregate BSA (heat denatured BSA assembles into amyloids but becomes more susceptible to digestion). FIG. 5B shows the solvent exposed peptides of the folded BSA protein are highly labeled but peptides of aggregates are less labeled. FIG. 5C shows total folded protein is more labeled than aggregate. FIG. 5D compares relative labeling of total protein (undigested) in a soluble or aggregate state as well as digested protein in the soluble or aggregate state.

Figure 8A:
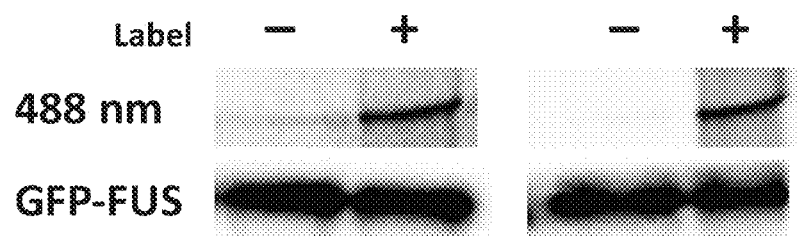
FIG. 8A shows purification of labeled protein. A protein of interest (GFP-FUS) can be immunopurified, fluorescence detected by SDS-PAGE, and protein levels determined by western blotting.
Figure 8B:
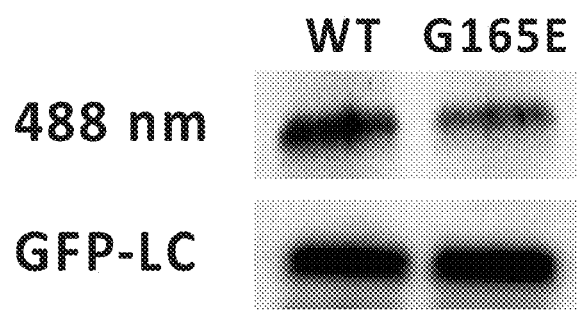
FIG. 8B shows FUS containing ALS-causing mutations (G165E) forms aggregates in the cell, which are resistant to chemical labeling.
Figure 8C:
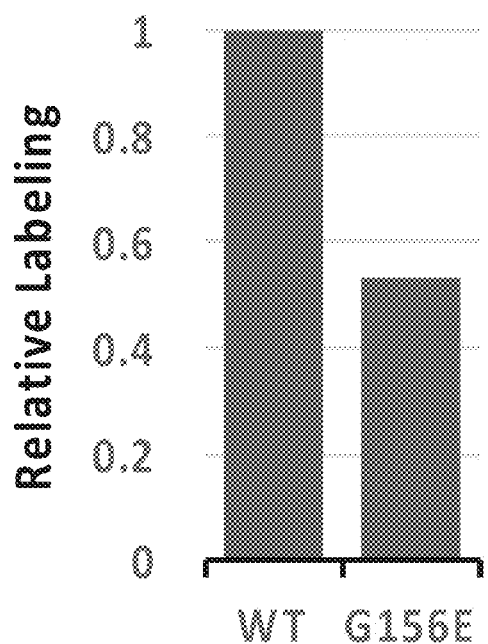
FIG. 8C shows relative labeling for the N-terminal LC domain, normalized to total protein by western blotting, reveals nearly 50% less labeling for ALS-mutant FUS.
Figure 9A:
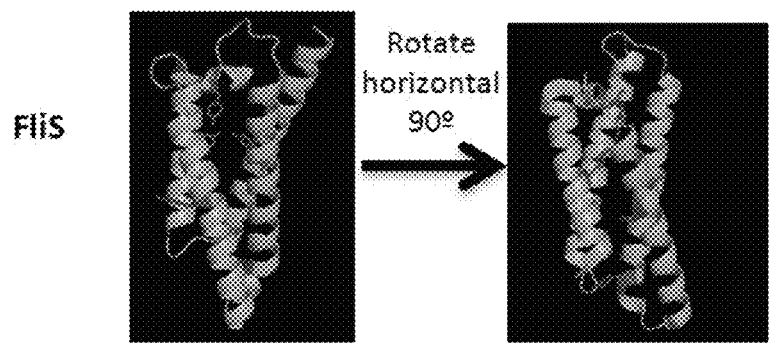
FIG. 9A shows the monomer form of FliS (pdb: 1ORJ).
Figure 9B:
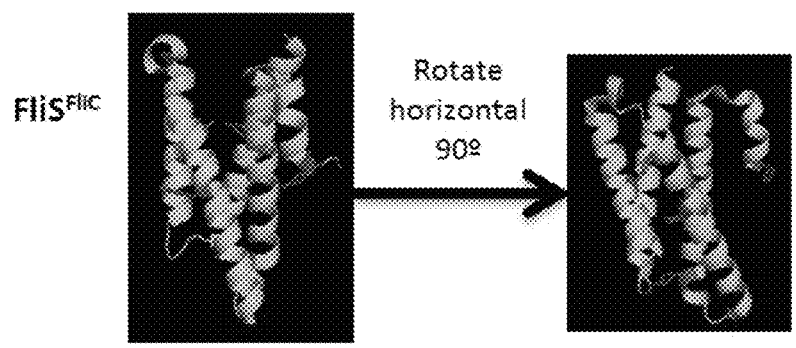
FIG. 9B shows the polymer form. Upon interacting with its partner FliC, the folding conformation changes and a helix containing a tyrosine residue is removed from the core to be exposed outside the protein (pdb: 1ORY).
Figure 10:
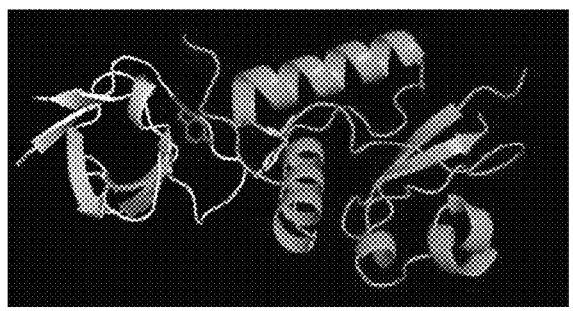
FIG. 10 shows two tyrosines become occluded once two different proteins interact—SH3 on the left (grey) and NEF on the right (green) (pdb: 1EFN).

FIG. 6 shows that few tyrosines in BSA are solvent exposed in the folded state. BSA (pdb: 4OR0) contains many tyrosines (top panels) that are buried and some that are solvent exposed. The surface models (bottom panels) of BSA conceal the buried tyrosines, revealing that they do not have access to the solvent. FIG. 7 shows total cellular protein can be labeled in cell lysate. Addition of TBD-conjugated to coumarin (TBD-C) labels proteins in total cell lysate. As a positive control, purified FUS and MBP are also labeled in solution. In the absence of TBD-C, no 488 nm fluorescence is detected. FIG. 8A shows purification of labeled protein. A protein of interest (GFP-FUS) can be immunopurified, fluorescence detected by SDS-PAGE, and protein levels determined by western blotting. FIG. 8B shows FUS containing ALS-causing mutations (G165E) forms aggregates in the cell, which are resistant to chemical labeling. FIG. 8C shows relative labeling for the N-terminal LC domain, normalized to total protein by western blotting, reveals nearly 50% less labeling for ALS-mutant FUS. FIG. 9A shows the monomer form of FliS (pdb: 1ORJ). FIG. 9B shows the polymer form. Upon interacting with its partner FITC, the folding conformation changes and a helix containing a tyrosine residue is removed from the core to be exposed outside the protein (pdb: 1ORY). Thus the protein FliS has 2 of 5 tyrosines exposed for labeling. The protein FliS$^{FliC}$ has 3 of 5 available for labeling, creating a clear quantifiable difference between the two states (see Goh et al., Curr Opin Struct Biol, 2004, 14:104-9). FIG. 10 shows two tyrosines become occluded once two different proteins interact—SH3 on the left (grey) and NEF on the right (green) (pdb: 1EFN). For SH3, the purple tyrosine is 1 of 3 in the protein, which becomes unable to be labeled after binding to NEF. For NEF, the gold tyrosine is 1 of 7 that becomes unable to be labeled after binding to SH3.

Figure 11:
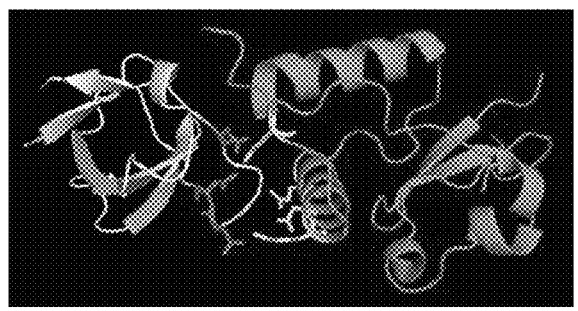
FIG. 11 shows reactive residues other than tyrosines that would become differentially targeted by chemical labeling upon the protein:protein interaction (highlighted purple for those one SH3 and yellow for those on NEF). These residues include arginines, lysines, glutamates, and aspartates.
Figure 12:
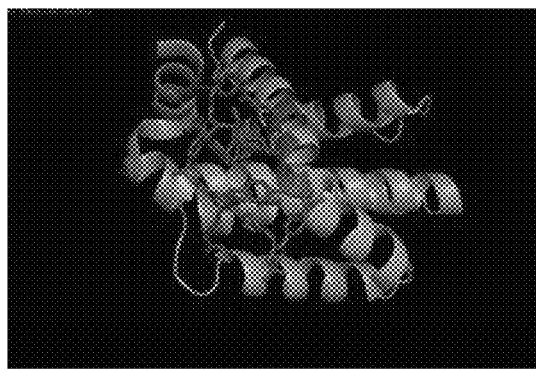
FIG. 12 shows the protein BCL-XL (green) has specific residues occluded by the small molecule inhibitor ABT-263 (red) (pdb: 4QNQ). This involves amino acid residues capable of labeling including tyrosines, arginines, and glutamates (highlighted blue).
Figure 13:
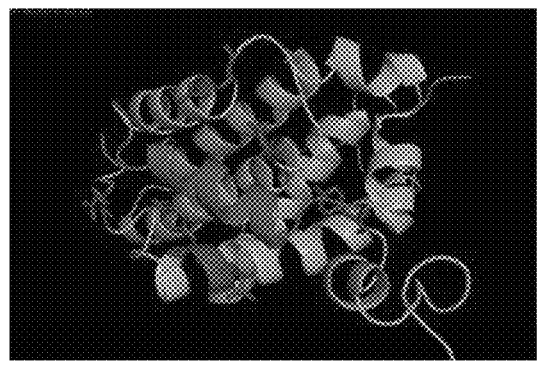
FIG. 13 shows the protein BCL-XL (green) has specific residues occluded by the peptide (red) BAK (pdb: 1BXL).

FIG. 11 shows reactive residues other than tyrosines that would become differentially targeted by chemical labeling upon the protein:protein interaction (highlighted purple for those one SH3 and yellow for those on NEF). These residues include arginines, lysines, glutamates, and aspartates. FIG. 12 shows the protein BCL-XL (green) has specific residues occluded by the small molecule inhibitor ABT-263 (red) (pdb: 4QNQ). This involves amino acid residues capable of labeling including tyrosines, arginines, and glutamates (highlighted blue). FIG. 13 shows the protein BCL-XL (green) has specific residues occluded by the peptide (red) BAK (pdb: 1BXL). This involves amino acid residues capable of labeling including tyrosines, arginines, and glutamates (highlighted blue). FIG. 14A and FIG. 14B shows the protein p65 (green) has specific residues occluded by a DNA molecule (pdb: 1RAM) (left). This involves amino acid residues capable of labeling including arginines and lysines (highlighted red right). FIG. 15 shows the potassium channel has specific residues occluded by the lipid interactions (pdb: 1BL8). This involves amino acid residues capable of labeling including arginines and tyrosines (highlighted blue). Changes in amino acid labeling due to lipid interactions can be potentiated by treatments with detergents, electrical voltage, or electrophysiological stimulation.

FIG. 16 shows sup35 yeast prion (pdb: 2OMP) with tyrosines (red arrows) occluded from chemical labeling in the aggregate form. FIG. 17 shows SOD1 (pdb: 1UXM) with an A4V mutation forms aggregates with lysines (pink) and aspartates (blue) either solvent exposed or occluded from chemical labeling in the aggregate state. FIG. 18 shows human prion protein (pdb: 4EII) forms amyloids with exposed cysteines (blue) available for chemical labeling. FIG. 19 shows islet amyloid polypeptide (IAPP, pdb: 3FTK) with tyrosines (red arrows) occluded from chemical labeling in the aggregate form. FIG. 20 shows the N-terminal amino acids up to the poly-Q region (pdb: 3I04) with lysines and glutamates (red) able to be chemically labeled to detect occlusion induced by expansion repeat associated aggregates. FIG. 21 shows alpha synuclein (pdb: 2N0A) with tyrosines and glutamates (red) and lysines (blue) able to become occluded from chemical labeling in the aggregate form. FIG. 22 shows human insulin amyloids (pdb: 2OMP) with tyrosines and glutamates (red arrows) occluded from chemical labeling in the aggregate form.

The present invention also features kits for detecting the presence of a protein of interest (e.g., associated with a proteopathy) in an aggregate form (or other folded state of interest). The kit may comprise a first reactive moiety conjugated to a first detectable label, the first reactive moiety is adapted to covalently modify label-able amino acids (e.g., tyrosines, cysteines, lysines, etc.) on the protein of interest, and a first reactive moiety conjugated to a second detectable label or a second reactive moiety conjugated to a second detectable label, the second reactive moiety is adapted to covalently modify label-able amino acids (e.g., tyrosines, cysteines, lysines, etc.) on the protein of interest, wherein the first detectable label and second detectable label are visually distinct. The detectable labels are adapted to be quantitated. In some embodiments, the kit further comprises a control sample. In some embodiments, the control sample comprises purified protein of interest.

Example 1

Example 1 describes a non-limiting method of the present invention. The protein Fused in sarcoma (FUS) exists in two forms, a free monomer and in assemblies wherein they are in a stacked n-sheet structure. The FUS aggregates cannot be observed by histological methods. FUS neuronal cytoplasmic inclusions (NCIs) have been observed in sporadic and non-SOD1 familial ALS patients by two independent studies. A histological study of skin biopsies showed a marked accumulation of FUS in keratinocytes with all tested sporadic ALS cases. However, two labs (including that of Inventors) did not find this in cultured fibroblasts of ALS patients. While histological analysis of skin biopsies has not been criticized for specificity, studies have shown them to suffer from low sensitivity and therefore reduced reliability in diagnosing neurodegenerative disease. TDP-43 is found in NCIs in more than 90% of ALS patients. Inclusions have also been noted in cultured fibroblasts and tissue-engineered skins. The repeated [S/G]Y[S/G] motifs are modeled as oriented in such a way that the tyrosines are stacked between the β-sheets forming π-stacking interactions that stabilize the polymeric structure. As FUS shifts to the assembled state, tyrosines become occluded. The present invention may feature comparing the labeling of the tyrosine residues to quantify the ratio of assembly for a protein of interest (e.g., FUS, TDP-43) and monomer protein of interest (e.g., FUS, TDP-43). Since the tyrosine residues become occluded as FUS shifts from the free state to the assembled state, the amount of labeling of aggregated FUS is reduced (as compared to FUS in the free state).

In some embodiments, the methods of the present invention comprise labeling molecule (e.g., exposed tyrosines) with label-conjugated aryl diazonium (the label may be, for example, a fluorescent label, quantum dot, radio label, etc.). In some embodiments, the protein of interest comprises FUS. In some embodiments, the protein of interest comprises TDP-43. In some embodiments, the assays can be quantitated by SDS-PAGE electrophoresis or by microplate assays. (Note the present invention is not limited to the aforementioned methods for quantitating the labeled protein. In some embodiments, the assay could be performed in fluid phase (e.g., platelet aggregation). In some embodiments, the present invention is used for monitoring thrombosis.)

In some embodiments, the present invention features using tagged proteins. e.g., GFP-FUS and GFP-TDP-43, stably integrated into cells, e.g., HeLa cells, e.g., for optimizing the assay. Without wishing to limit the present invention to any theory or mechanism, it is believed that using HeLa or similar cells may be advantageous for assay optimization because they divide rapidly. Without wishing to limit the present invention to any theory or mechanism, it is believed that using a GFP-tag or similar tag may be advantageous for assay optimization because it allows for convenient and high throughput pull down assays.

Example 2

Example 2 describes non-limiting methods, systems, and compositions for determining the extent and changes in conformations and protein/nucleic acid conformations in cells or in a test tube. Tissues, cells, or lysates thereof may be exposed to titrating concentrations of denaturant or detergent. Strong interactions will maintain their natural labeling levels in higher concentrations of denaturant. As the protein-protein or protein-nucleic acid complexes disassemble, chemical labeling may be increased or decreased for proteins, nucleic acids, or substrates are released from the complexes or cellular granules. As molecules denature, chemical labeling also may be increased or decreased, depending on the particular folding state of that molecule. As proteins denature, they may fall into an aggregate state and chemical labeling may be decreased. Each change in labeling may be indicative of changes in protein or nucleic acid interactions, structure, conformations, or folding. Purified proteins, nucleic acids, or other binding substrates may be exposed to titrating concentrations of denaturant or detergent. Strong interactions will maintain their natural labeling levels in higher concentrations of denaturant. As the protein-protein or protein-nucleic acid complexes disassemble, chemical labeling may be increased or decreased for proteins, nucleic acids, or substrates are released from the complexes or cellular granules based on whether new surfaces are exposed or a particular conformation collapses. As proteins denature, chemical labeling also may be increased or decreased, depending on whether the label is hydrophilic (labeling the molecule exterior) or hydrophobic (labeling the molecule interior). As proteins denature, they may fall into an aggregate state and chemical labeling may be decreased. Each change in labeling may be indicative of changes in protein or nucleic acid interactions, structure, conformations, or folding.

Example 3

Example 3 describes non-limiting methods, systems, and compositions for the use of fluorescence as a chemical label. Proteins or nucleic acids may be chemically labeled with an appropriate chemistry (PTAD, diazerine, maleimide, NHS, thiol, etc.). The chemical molecules may be pre-conjugated to fluorescent molecules or the chemical molecules could be modified with an appropriate reactive group (amine, carboxyl, azide, alkyne, etc.) for conjugation after labeling the biomolecule or molecules of interest. As a control to increase sensitivity, following labeling of the initial or native state, biomolecules may be denatured and remaining reactive groups, nucleotide bases, or residues labeled by the same or alternate chemistry and with an alternate fluorescent or detectable label. Fluorescent biomolecules may be detected in bulk or isolated using standard purification techniques, including but limited to chromatography, electrophoresis, affinity purification, immunopurification, etc. Fluorescence may be (1) detected in solution, (2) following separation of unconjugated chemical label by standard techniques such as dialysis, centrifugation, desalting, chromatography, or electrophoresis, (3) following immobilization of the protein, nucleic acid, or biomolecule, on a substrate such as nitrocellulose, PDVF, antibodies, biomolecular substrates, high binding multi-well plates, conjugated beads, etc., or (4) following digestion with proteases or nucleases and separation by electrophoresis, capillary electrophoresis, or fractionation. Fluorescence may be measured by standard techniques including spectrometry, plate reader, anisotropy, laser induced fluorescence (e.g. capillary zone electrophoresis and laser induced fluorescence, CZE-LIF), TIRF, fluorescence or confocal microscopy, photoelectron multiplier detection, luminescence, CCD camera, etc. Fluorescence may be compared to that of biomolecules in an alternate state of binding, free, aggregate, disaggregate, folded, partially unfolded, fully denatured, conformation, or amyloid. Fluorescence of a single molecule may be compared to the level of labeling of the same with an alternate label, such as a fluorophore of different wavelengths.

Example 4

Example 4 describes non-limiting methods, systems, and compositions for the use of radioactivity as a chemical label. Proteins or nucleic acids may be chemically labeled with an appropriate chemistry (PTAD, diazerine, maleimide, NHS, thiol, etc.). The chemical molecules may be pre-conjugated to radioactive molecules ($^{32}P$, $^{13}C$, $^{3}H$, etc.) or the chemical molecules could be modified with an appropriate reactive group (amine, carboxyl, azide, alkyne, etc.) for conjugation after labeling the biomolecule or molecules of interest. As a control to increase sensitivity, following labeling of the initial or native state, biomolecules may be denatured and remaining reactive groups, nucleotide bases, or residues labeled by the same or alternate chemistry and with an alternate fluorescent or detectable label. Radioactive biomolecules may be detected in bulk or isolated using standard purification techniques, including but limited to chromatography, electrophoresis, affinity purification, immunopurification, etc. Radioactivity may be (1) detected in solution, (2) following separation of unconjugated chemical label by standard techniques such as dialysis, centrifugation, desalting, chromatography, or electrophoresis, (3) following immobilization of the protein, nucleic acid, or biomolecule, on a substrate such as nitrocellulose, PDVF, antibodies, biomolecular substrates, high binding multi-well plates, conjugated beads, etc., or (4) following digestion with proteases or nucleases and separation by electrophoresis, capillary electrophoresis, or fractionation. Radioactivity may be measured by standard techniques including scintillation, phosphorescence, radiometry, photo film, etc. Radioactivity may be compared to that of biomolecules in an alternate state of binding, free, aggregate, disaggregate, folded, partially unfolded, fully denatured, conformation, or amyloid. Radioactivity of a single molecule may be compared to the level of labeling of the same with an alternate label, such as a fluorescence or western analysis. The use of radiolabels may be beneficial for circumstances wherein protein numbers are very small (enhanced sensitivity with radiolabels), e.g., in a patient sample with low protein numbers, e.g., a circumstance when fluorescence is not sensitive enough, etc.

Example 5

Example 5 describes non-limiting methods, systems, and compositions for the use of NMR labels as a chemical label. Proteins or nucleic acids may be chemically labeled with an appropriate chemistry (PTAD, diazerine, maleimide, NHS, thiol, etc.). The chemical molecules may be pre-conjugated to isotopic molecules ($^2H$, $^{19}F$, $^{15}N$, $^{13}C$, etc.) or the chemical molecules could be modified with an appropriate reactive group (amine, carboxyl, azide, alkyne, etc.) for conjugation after labeling the biomolecule or molecules of interest. As a control to increase sensitivity, following labeling of the initial or native state, biomolecules may be denatured and remaining reactive groups, nucleotide bases, or residues labeled by the same or alternate chemistry and with an alternate isotopic or detectable label. Isotopically labeled biomolecules may be detected in bulk or isolated using standard purification techniques, including but limited to chromatography, electrophoresis, affinity purification, immunopurification, etc. Isotopically labeled samples may be (1) detected in solution, (2) following separation of unconjugated chemical label by standard techniques such as dialysis, centrifugation, desalting, chromatography, or electrophoresis, (3) following immobilization of the protein, nucleic acid, or biomolecule, on a substrate such as nitrocellulose, PDVF, antibodies, biomolecular substrates, high binding multi-well plates, conjugated beads, etc., or (4) following digestion with proteases or nucleases and separation by electrophoresis, capillary electrophoresis, or fractionation. Isotopic labeling and chemical shifts may be measured by standard NMR spectroscopy. Isotopic may be compared to that of biomolecules in an alternate state of binding, free, aggregate, disaggregate, folded, partially unfolded, fully denatured, conformation, or amyloid. Isotopic labeling of a single molecule may be compared to the level of labeling of the same with an alternate label or uniform isotopic labeling of the entire biomolecule.

Example 6

Example 6 describes non-limiting methods, systems, and compositions for the use of contrast agents as a chemical label. Proteins or nucleic acids may be chemically labeled with an appropriate chemistry (PTAD, diazerine, maleimide, NHS, thiol, etc.). The chemical molecules may be pre-conjugated to molecules bound to contrast agents (Gd, iron oxide, iron platinum, Mn, etc) or the chemical molecules could be modified with an appropriate reactive group (amine, carboxyl, azide, alkyne, etc.) for conjugation after labeling the biomolecule or molecules of interest. Labeled biomolecules may be detected in animals or humans using standard MRI. MRI images may be compared to that of control animals or humans possessing an alternate state of binding, free, aggregate, disaggregate, folded, partially unfolded, fully denatured, conformation, or amyloid.

Example 7

Example 7 describes non-limiting methods, systems, and compositions for the use of chemical labels for detection by mass spectrometry. Proteins or nucleic acids may be chemically labeled with an appropriate chemistry (PTAD, diazerine, maleimide, NHS, thiol, etc.). The chemical molecules may be pre-conjugated to ionizable or bulky molecules or the chemical molecules could be modified with an appropriate reactive group (amine, carboxyl, azide, alkyne, etc.) for conjugation after labeling the biomolecule or molecules of interest. As a control to increase sensitivity, following labeling of the initial or native state, biomolecules may be denatured and remaining reactive groups, nucleotide bases, or residues labeled by the same or alternate chemistry and with an alternate label with differing molecular weight or ionization potential. Labeled biomolecules may be detected in bulk or isolated using standard purification techniques, including but limited to chromatography, electrophoresis, affinity purification, immunopurification, etc. Labeling may be (1) detected in solution, (2) following separation of unconjugated chemical label by standard techniques such as dialysis, centrifugation, desalting, chromatography, or electrophoresis, (3) following immobilization of the protein, nucleic acid, or biomolecule, on a substrate such as nitrocellulose, PDVF, antibodies, biomolecular substrates, high binding multi-well plates, conjugated beads, etc., or (4) following digestion with proteases or nucleases and separation by electrophoresis, capillary electrophoresis, or fractionation. Labeling may be measured by standard mass spectrometry techniques including LC MS-MS, LC-MS, MALDI-TOF, etc. Samples may be measured with or without protease or nuclease digestion. Labeling will result in a difference in molecular weight for biomolecules or fragments thereof of differing extent depending on the degree of labeling. The extent of labeling may be compared to that of biomolecules in an alternate state of binding, free, aggregate, disaggregate, folded, partially unfolded, fully denatured, conformation, or amyloid. Labeling of a single molecule may be compared to the level of labeling of the same with an alternate label, such as labels of differing molecular weight or ionization potential.

Example 8

Example 8 describes non-limiting examples of proteins (e.g., tyrosine rich fragments of proteins) with tyrosines that may be used as labeling targets and methods of identification of said targets.

The identity of solvent exposed or buried tyrosines for a protein or a specific protein conformation may be known based on solved structures, or may be determined de novo for proteins of interest. One rapid method to monitor this would be fluorescent or radio-isotopic labeling of tyrosines in solution or in the cellular environment and detection by standard respective techniques. The examples herein have glycine/tyrosine and serine/tyrosine rich sequences from the human proteome. Among these, attractive target sequences may include: low complexity sequences; glycine and/or proline rich sequences; or lysine, arginine, glutamate, or aspartate rich sequences. Such sequences are likely or known to be either intrinsically disordered and/or solvent exposed for labeling. The structural properties and binding surfaces for such intrinsically disordered domains and proteins are challenging, labor intensive (e.g., limited to low throughput), if not impossible to study with standard structural biology techniques, including x-ray crystallography, NMR, and mass spectrometry. Tyrosine rich sequences can become unfolded and enter into amyloid or amyloid-like aggregates that are resistant or impervious to cellular mechanisms to degrade proteins and protein aggregates. The extent of amyloid or amyloid-like aggregation accumulating in cells can be monitored by chemical labeling, which is altered by reduction of solvent accessibility and/or a greater extent of tyrosines engaged in pi-pi stacking interactions due to the stacked beta-sheet structures formed.

Two non-limiting examples, HNRNPR and FUS, possess intrinsically disordered, low-complexity domains known to be involved in polymerization and formation of higher order assemblies known as droplets, hydrogels, or phase-separated liquid droplets, and, in cells, comprise granular bodies or non-membrane bound organelles. Such assemblies may be induced in cells in response to stimuli such as DNA damage or oxidative stress, and may mistakenly proceed into aggregates under conditions of proteins possessing certain genetic mutations, or other disruptions or imbalances in cellular response pathways, such as the autophagy or unfolded-response pathways. The in vitro equilibria or normal cellular response of proteins entering and exiting assemblies may be monitored in bulk by changes in tyrosine labeling. The extent of granular proteins entering into irreversible aggregates may be monitored by the reduction in relative labels of chemical labeling. Amino acids 301 to 494 of HNRNPR (HGNC:5047) contain about 24 tyrosines, e.g., positions 319, 321, 325, 326, 328, 331, 332, 335, 336, 338, 340, 343, 347, 351, 352, 354, 358, 390, 439, 471, 475, 477, 485, 498) and one or more of said tyrosines may be a target for chemical labeling. About 27 tyrosines are present in amino acids 1-212 of FUS (HGNC:4010), e.g., positions 6, 14, 17, 25, 33, 38, 41, 50, 55, 58, 66, 75, 81, 91, 97, 100, 113, 122, 130, 136, 143, 149, 155, 161, 177, 194, 208, and one or more of said tyrosines may be a target for chemical labeling.

Cellular granules comprised of tyrosine rich, low-complexity domain proteins may be isolated and their sizes, density, and unique underlying structure measured by fluorescent or radio-isotopic labeling of tyrosines in cells or cell lysates and lysates subjected to standard biochemical purification, including, but not limited to, immuno- or affinity-purification, centrifugation, ultra centrifugation, size-exclusion filtration, SDD-AGE, or size-exclusion chromatography.

Another example, THRAP3 (HGNC:22964), can undergo large structural changes following introduction of thyroid hormone to cells. This shift and the extent of thyroid hormone induced folding or protein interactions can be monitored by determining the extent of chemical labeling of tyrosines. (Amino acids 1-120 of THRAP3 have approximately 11 tyrosines, e.g., positions 54, 68, 80, 84, 85, 94, 99, 104, 107, 114, 118, and one or more of said tyrosines may be a target for chemical labeling). Another example, POLR2A (HGNC:9187), possesses multiple repeats of a peptide sequence containing tyrosines, known as the C-terminal domain, CTD. (Amino acids 1558-1842 or POLR2A have approximately 37 tyrosines, e.g., positions 1561, 1581, 1593, 1660, 1608, 1615, 1622, 1629, 1636, 1643, 1650, 1657, 1664, 1671, 1678, 1685, 1692, 1699, 1706, 1713, 1720, 1727, 1734, 1741, 1748, 1755, 1762, 1769, 1776, 1783, 1790, 1797, 1804, 1811, 1818, 1825, 1832, and one or more of said tyrosines may be a target for chemical labeling) This sequence is known to be alternately bound by different kinases and RNA processing factors as the polymerase engages in the process of RNA transcription. The extent of chemical modification of exposed tyrosines can monitored to reveal protein interactions with the CTD as the polymerase proceeds through the act of transcription. In vitro, the rates and extent of protein factor binding to the CTD can be determined by monitoring the relative extent of tyrosine labeling in titrating amounts of CTD-binding proteins.

Another example, FAM98B (HGNC:26773), contains tyrosines within an RGG/RG RNA-binding domain. (Amino acids 331-433 of FAM98B contain 6 tyrosines, e.g., positions 393, 399, 405, 414, 430, 433, and one or more of said tyrosines may be a target for chemical labeling). The extent of FAM98B binding to RNA can be monitored by monitoring the extent of tyrosine labeling in titrating amounts of RNA. Another example, KRTAP20-1 (HGNC:18943), is a keratin-associated protein. (Amino acids 1-56 have 17 tyrosines, e.g., positions 3, 4, 7, 8, 11, 13, 20, 27, 31, 34, 37, 41, 42, 47, 50, 53, 56, and one or more of said tyrosines may be a target for chemical labeling) Many if not most keratin proteins assemble into rigid polymers. Monitoring relative levels of tyrosine labeling can reveal the extent of keratin polymerization, misfolding, excretion, and degradation, as well as the relative or absolute amounts of keratinocytes, degradation, or death in populations of tissue derived samples, in solution, cell culture, or following FACS sorting.

Another example, sourcin (SRI, HGNC:11292) has 5 tyrosines within amino acids 10-38, e.g., positions 13, 14, 18, 36, 38, and one or more of said tyrosines may be a target for chemical labeling. Other examples of proteins with tyrosine rich domains include but are not limited to: HNRPH1 (HGNC:5041), KRTAP19-1 (HGNC:18936), ELN (HGNC:3327), DHX9 (HGNC:2750), EBF4 (HGNC:29278), CIRBP (HGNC:1982), DHX36 (HGNC:14410), HNRNPA1 (HGNC:5031), KLF2 (HGNC:6347), HNRNPA3 (HGNC:24941), PEF1 (HGNC:30009), HNRNPA1L2 (HGNC:27067), NCBP2 (HGNC:7659), TMBIM1 (HGNC:23410), AKAP8 (HGNC:378), DAZAP1 (HGNC:2683), KRT10 (HGNC:6413), PBX2 (HGNC:8633), ASMTL (HGNC:751), HNRNPH3 (HGNC:5043), CLASRP (HGNC:17731), ATRNL1 (HGNC:29063), DDX3X (HGNC:2745), TAF15 (HGNC:11547), HNRNPA2B1 (HGNC:5033), ILF3 (HGNC:6038), TNXB (HGNC:11976), CUX2 (HGNC:19347), FBN1 (HGNC:3603), etc., and one or more of said tyrosines or other label-able amino acids may be a target for chemical labeling.

Example 9

Example 9 describes non-limiting examples of proteins (e.g., cysteine rich fragments of proteins) with cysteines that may be used as labeling targets and methods of identification of said targets.

The identity of solvent exposed or buried cysteines for a protein or a specific protein conformation may be known based on solved structures, or may be determined de novo for proteins of interest. One rapid method to monitor this would be fluorescent or radio-isotopic labeling of cysteines in solution or in the cellular environment and detection by standard respective techniques.

Examples herein have glycine/cysteine rich sequences from the human proteome. Among these, attractive target sequences may include: low complexity sequences; glycine and/or praline rich sequences; or lysine, arginine, glutamate, or aspartate rich sequences. Such sequences are likely to be either intrinsically disordered and/or solvent exposed for labeling. The structural properties and binding surfaces for such intrinsically disordered domains and proteins are challenging, labor intensive (e.g., limited to low throughput), if not impossible to study with standard structural biology techniques, including x-ray crystallography, NMR, and mass spectrometry.

As an example, IGFBP1 (HGNC:5469) has a disordered N-terminus and a C-terminal fold for which the structure has been solved (e.g. pdb 1ZT3) revealing solvent exposed cysteines engaged in disulfide bonds. Fluorescent labeling of these in following treatment with reducing and non-reducing conditions provides a rapid, high-throughput method to monitor protein refolding, revealing the extent of misfolding or the rate of folding at a population level. (Amino acids 1-86 and 175-259 of IGFBP1 have 11 and 6 cysteines, respectively, e.g., positions 30, 33, 41, 48, 57, 59, 60, 63, 71, 78, 84, 176, 206, 217, 228, 230, 251, and one or more of said cysteines may be a target for chemical labeling). For Znf74 (HGNC:13144), the cysteines are structurally important as some coordinate a zinc ion. As the protein denatures or the zinc is otherwise lost, these cysteines become free for labeling. Fluorescence labeling of these zincs creates an attractive technique to screen for protein stability. (ZNF74 has about 10 cysteines out of 212 amino acids, e.g., positions 23, 53, 55, 76, 86, 96, 160, 167, 174, 181, and one or more of said cysteines may be a target for chemical labeling) The cell surface receptor Cr1L (HGNC:2335) is known to present labile cysteines at the cell surface for immune cells, such as splenocytes, during immune response, making them available for labeling. Fluorescence labeling of these cysteines pose attractive targets for subsequent separation of immune responsive cells by FACS sorting. (CR1L has about 32 cysteines out of 539 amino acids, e.g., positions 35, 65, 78, 91, 96, 123, 137, 153, 158, 187, 207, 224, 230, 258, 272, 285, 289, 318, 332, 343, 350, 378, 392, 408, 413, 440, 454, 470, 475, 504, 541, 567, and one or more of said cysteines may be a target for chemical labeling).

Other examples of proteins with cysteine rich domains include but are not limited to: IGFBP3 (HGNC:5472), TNXB (HGNC:11976) (58 cysteines within amino acids 301-600, e.g., positions 306, 311, 315, 321, 326, 328, 337, 342, 346, 352, 357, 359, 368, 373, 377, 383, 388, 390, 399, 404, 408, 414, 419, 421, 430, 435, 439, 445, 450, 452, 461, 466, 470, 476, 481, 483, 492, 497, 501, 507, 512, 514, 523, 528, 532, 538, 543, 545, 554, 559, 563, 569, 574, 576, 585, 590, 594, 600), RAB17 (HGNC:16523) (3 cysteines within amino acids 39-49, e.g., positions 39, 47, 49), RAB14 (HGNC:16524) (2 cysteines at the C-terminus, e.g., positions 213, 215). CCER1 (HGNC:28373) (2 cysteines within amino acids 15-23 and 1 at amino acid 295, e.g., positions 22, 24, 295), KRTAP19-5 (HGNC:18940) (4 cysteines within amino acids 1-72, e.g., 27, 29, 58, 62), WISP2 (HGNC:12770) (4 cysteines within amino acids 48-59, 3 cysteines within amino acids 115-127, and 2 cysteines within amino acids 155-160, e.g., positions 50, 52, 53, 56, 117, 121, 123, 157, 158), CYR61 (HGNC:2654) (38 cysteines within amino acids 1-381, e.g., positions 26, 30, 32, 39, 50, 52, 53, 56, 64, 70, 78, 91, 100, 117, 121, 123, 130, 134, 145, 157, 158, 163, 229, 239, 243, 258, 267, 272, 286, 303, 314, 317, 322, 323, 337, 353, 355, 359), NOTCH4 (HGNC:7884), BMP2 (HGNC:1069), FBXO24 (HGNC:13595), WDR59 (HGNC:25706), CHRNAI (HGNC:1955), LCE4A (HGNC:16613), RAB43 (HGNC:19983), EDA (HGNC:3157), LCK (HGNC:6524), TF (HGNC:11740), KRTAP21-1 (HGNC:18945), IGFBP2 (HGNC:5471), MEGF6 (HGNC:3232), SLC5A12 (HGNC:28750), etc., and one or more of said cysteines or other label-able amino acids may be a target for chemical labeling.

Example 10

Example 10 describes non-limiting examples of markers that may be useful for detecting aggregation in ALS patient tissues or in vitro samples, or frontotemporal lobar degeneration (FTLD) (e.g., ALS-related markers or FTLD-related markers that may be targets for chemical labeling).

TDP-43, FUS, and hnRNPA1 are non-limiting examples or markers with tyrosines that may be considered key targets for labeling to identify aggregation. For example, TDP-43 (HGNC:11571) has a tyrosine at position 4, 43, 73, 77, and 374, and one or more of said tyrosines may be useful for evaluation of labeling. FUS (HGNC:4010) has a tyrosine at position 6, 14, 17, 25, 33, 38, 41, 50, 55, 58, 66, 75, 81, 91, 97, 100, 113, 122, 130, 136, 143, 149, 155, 161, 177, 194, 208, and one or more of said tyrosines may be useful for evaluating labeling. HnRNPA1 (HGNC:5031) has a tyrosine at position 244, 260, 266, 189, 195.305, 314, and one or more of said tyrosines may be targeted for labeling. GRN (HGNC:4601) is a non-limiting example of a cysteine rich protein for which cysteines may be important targets for detecting aggregation. GRN has a cysteine at position 20, 26, 30, 31, 41, 42, 61, 67, 73, 83, 84, 92, 98, 99, 105, 112, 126, 133, 139, 140, 149, 150, 157, 158, 164, 165, 171, 178, 208, 215, 221, 222, 231, 232, 239, 240, 246, 247, 253, 260, 284, 290, 296, 297, 306, 307, 314, 315, 321, 322, 328, 335, 366, 372, 378, 379, 388, 389, 396, 397, 403, 404, 410, 416, 444, 450, 456, 457, 466, 467, 474, 475, 481, 482, 488, 495, 521, 527, 533, 534, 543, 544, 551, 552, 558, 559, 565, and 572, and one or more of said cysteines may be useful for evaluating labeling.

SQSTM1 (HGNC:11280) is an example of a diverse amino acid sequence with multiple amino acids available for chemical labeling to detect aggregation. For example, SQSTM1 has a tyrosine at position 89, 98, 140, 148, 422; a lysine at position 91, 100, 102, 103, 141; and a cysteine at position 105, 113, 128, 131, 142, 145, 151, 154, and one or more of said amino acids may be targets for detecting aggregation. SOD1 (HGNC:11179) has several amino acids that may be of interest as targets, e.g., lysines at position 4, 10, 24, 31, 37, 71, 76, 92, 123, 129, and/or 137, and/or aspartic acid at positions 12, 53, 77, 84, 91, 93, 97, 102, 110, 125, and/or 126, and one or more of said amino acids may be targets for labeling.

Other proteins that may be useful for detecting aggregation, e.g., related to ALS, may include but are not limited to PFN1 (HGNC:8881), VCP (HGNC:12666), OPTN (HGNC:17142), SETX (HGNC:445), ANG (HGNC:483), hnRNPA2B1 (HGNC:5033), and UBQLN2 (HGNC:12509). For example, one or more label-able amino acids in said proteins may be used as targets for labeling.

Example 11

Example 11 describes non-limiting examples of markers that may be useful for detecting aggregation in tissues of patients with a particular proteopathy (or in vitro samples), e.g., proteopathy-related markers that may be targets for chemical labeling).

APP and Tau are non-limiting examples of markers that may be useful for detecting aggregation (e.g., in a patient sample, in vitro, etc.) related to Alzheimer's disease or other related diseases such as but not limited to chronic traumatic encephalopathy, etc. For example, APP (HGNC:620) is an aggregating protein with 3 tyrosine rich regions and two cysteine rich regions. These may be useful targets for detecting aggregation by chemical labeling. For example, tyrosines at positions 72, 77, 115, 168, 572, 588, 681, 728, 757, and/or 762, and/or cysteines at positions 73, 98, 105, 117, 158, and/or 174 may be targets for detecting aggregation or protein folding states. Tau (HGNC:6893) is a lysine rich protein with multiple regions that may be useful for targeting with chemical labeling. For example, lysines at positions 366, 375, 381, 383, 391, 392, 394, 402, 405, 413, 440, 455, 458, 460, 465, 467, 480, 666, 675, 678, 682, 688, 704, 705, 710, 718, and/or 720 may be targets for detecting aggregation or protein folding states. Other non-limiting examples of markers that may be useful for detecting aggregation related to Alzheimer's disease or other related diseases (such as but not limited to chronic traumatic encephalopathy, etc.) may include APPBP2 (HGNC:622), APCS (HGNC:584), APBA2 (HGNC:579), PSEN1 (HGNC:9508), and PSEN2 (HGNC:9509).

HTT (HGNC:4851) is a non-limiting example of a marker that may be useful for detecting aggregation (e.g., in a patient sample, in vitro, etc.) related to Huntington's disease. For example, lysines and/or cysteines of HTT may be targets for detecting aggregation by chemical labeling. For example, lysines at positions 6, 9, 15, 91, 92, 98, and/or 99, and/or cysteines at positions 105 and/or 109 may be targets.

Alpha-synuclein, NEFL light chain (HGNC:7739) and NEFL medium chain (NP001099011.1) are non-limiting examples of markers that may be useful for detecting aggregation related to Parkinson's disease. For example, alpha synuclein (SNCA, HGNC:11138) is a lysine rich and tyrosine rich protein, and said lysines and/or tyrosines may be targets for detecting aggregation by chemical labeling. For example, lysines at positions 6, 10, 12, 21, 23, 32, 34, 43, 45, 58, and/or 60, and/or tyrosines at positions 125, 133, and/or 136 may be targets. For NEFL light chain, lysines at positions 84, 91, and/or 116, and/or tyrosines at positions 6, 9, 10, 14, 18, 33, 40, 43, and/or 57 may be targets.

Proteopathies may include some cancers. For example, p53 (HGNC:11998) is a protein that may be prone to aggregation in some cancers. Tyrosines at positions 103, 107, and/or 126 may be targets for detecting aggregation by chemical labeling. IAPP HGNC:5329) is an aggregating protein in type 2 diabetes. Its lysines (e.g., positions 5, 21, 32, 34, 72 and/or 80) may be used as a target for chemical labeling to detect aggregation. For insulin amyloidosis, insulin (HGNC:6081) may be a target for chemical labeling to detect aggregation (e.g., cysteines at positions 31, 43, 95, 96, 100 and/or 109). For kidney dialysis amyloidosis, B2M (HGNC:914) may be a target for chemical labeling to detect aggregation (e.g., lysines at positions 26, 43, 50, 60, 77, 93, and/or 96, and/or tyrosines at positions 30, 65, 68, 69, and/or 90). For Creutzfeldt-Jakob disease, PrP (HGNC:9449) may be a target for chemical labeling to detect aggregation (e.g., tyrosines at positions 128, 145, 149, 150, 157, 162, 163, 169, 218, 225 and/or 226, and/or lysines, etc.)

The present invention is not limited to the any of the amino acids and/or residue numbers disclosed herein for targeting chemical labeling.

The disclosures of the following U.S. Patents are incorporated in their entirety by reference herein: U.S. Pat. No. 62/203,725 and U.S. patent Ser. No. 14/918,287.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of detecting the presence of occluded amino acids in a protein associated with a proteopathy in a test sample, said method comprising:
   a. subjecting the test sample to a reaction adapted to covalently modify tyrosines with a first reactive moiety conjugated to a first detectable label;
   b. subjecting the test sample to denaturing conditions after labeling the sample with the first reactive moiety conjugated to the first detectable label;
   c. subjecting the test sample to a reaction adapted to covalently modify tyrosines with the first reactive moiety conjugated to a second detectable label after subjecting the sample to denaturing conditions, wherein the first detectable label and second detectable label are visually distinct; and
   d. making visible the first detectable label and second detectable label;
   wherein the presence of the second detectable label in addition to the first detectable label is indicative of the presence of occluded tyrosines in the protein associated with a proteopathy in the test sample.

2. The method of claim 1, wherein the presence of occluded amino acids in the protein associated with a proteopathy in the test sample is indicative of a presence of a proteopathy.

3. The method of claim 1, wherein the proteopathy is Alzheimer's disease, Parkinson's disease, Creutzfeldt-Jacob disease, prion disease, an amyloidosis, Huntington's disease, frontotemporal lobar degeneration (FTLD), type 2 diabetes, a cancer associated with p53 aggregation, amyotrophic lateral sclerosis (ALS), chronic traumatic encephalopathy, dementia, tauopathies, retinal ganglion cell degeneration, cerebral beta amyloid angiopathy, Alexander disease, cerebral hemorrhage with amyloidosis, CADASIL, seipinopathies, familial amyloidotic neuropathy, senile systemic amyloidosis, cataracts, medullary thyroid carcinoma, pituitary prolactinoma, cystic fibrosis, sickle cell disease, or pulmonary alveolar proteinosis.

4. The method of claim 1, wherein the protein associated with a proteopathy is selected from fused in sarcoma (FUS), TDP-43, hnRNPA1, GRN, SQSTM1, SOD1, PFN1, VCP, OPTN, SETX, ANG, hnRNPA2B1, UBQLN2, APP, Tau, APPBP2, APCS, APBA2, PSEN1, PSEN2, HTT, Alpha-synuclein, NEFL light chain, NEFL medium chain, p53, IAPP, insulin, B2M, PrP, or a combination thereof.

5. The method of claim 1, wherein the first detectable label or second detectable label comprises coumarin, fluorophores, radiolabels, heavy isotopes, metal chelators, biotin, peptides, fluorescent microspheres, fluorescent proteins, quantum dots, or a combination thereof.

6. The method of claim 1, wherein occluded amino acids are associated with a protein in a bound state.

7. The method of claim 1, wherein occluded amino acids are associated with a protein in a folded state.

8. The method of claim 1, wherein occluded amino acids are associated with a protein in an interactive state wherein the protein interacts with a second molecule.

9. The method of claim 1, wherein making visible the detectable label comprises subjecting the sample to fluorescence spectroscopy, imaging, NMR, chromatography, electrophoresis, affinity purification, immunopurification, or a combination thereof.

10. The method of claim 1, wherein the first reactive moiety comprises 4-phenyl-3H-1,2,4-triazole-3,5(4H)-dione (PTAD) or a diazonium compound.

11. The method of claim 1, wherein the reaction adapted to covalently modify tyrosines with the first reactive moiety conjugated to the first detectable label comprises 4-phenyl-3H-1,2,4-triazole-3,5(4H)-dione (PTAD) chemistry.

12. The method of claim 1, wherein the reaction adapted to covalently modify tyrosines with the first reactive moiety conjugated to the first detectable label comprises diazonium chemistry.

* * * * *